United States Patent
Jacobsen et al.

(10) Patent No.: US 7,247,766 B2
(45) Date of Patent: Jul. 24, 2007

(54) DOUBLE TRANSGENIC MICE OVEREXRESSING HUMAN BETA SECRETASE AND HUMAN APP-LONDON

(75) Inventors: Helmut Jacobsen, Schopfheim (DE); Laurence Mosbach-Ozmen, Saint-Louis (FR); Peter Nelboeck-Hochstetter, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 196 days.

(21) Appl. No.: 10/372,730

(22) Filed: Feb. 24, 2003

(65) Prior Publication Data
US 2003/0167486 A1  Sep. 4, 2003

(30) Foreign Application Priority Data
Mar. 1, 2002  (EP) .................. 02004331

(51) Int. Cl.
*A01K 67/027* (2006.01)
*A01K 67/033* (2006.01)
*C12N 15/63* (2006.01)
*G01N 33/15* (2006.01)

(52) U.S. Cl. ............... 800/18; 800/3; 800/12; 800/22; 800/25; 435/354

(58) Field of Classification Search ............ 800/8, 800/9, 12, 13, 14, 21, 22
See application file for complete search history.

(56) References Cited

U.S. PATENT DOCUMENTS
4,736,866 A   4/1988 Leder et al.

OTHER PUBLICATIONS

Wall (1996) Transgenic Livestock: progress and prospects. Theriogenology 45:57-68.*
Gilbert in Developmental Biology, fifth edition, 1997, Sinauer Associates, Inc., Sunderland, MA, pp. 69-72.*
Sigmund CD. Viewpoint: are studies in genetically altered mice out of control? Arterioscler Thromb Vasc Biol. Jun. 2000;20(6):1425-9.*
Lehman et al. Genetic background regulates beta-amyloid precursor protein processing and beta-amyloid deposition in the mouse. Hum Mol Genet. Nov. 15, 2003;12(22):2949-56.*
Hock et al. Transgenic mouse models of Alzheimer's disease. Trends Genet. Oct. 2001;17(10):S7-12.*
Richards FM. Protein stability: still an unsolved problem. Cell Mol Life Sci. Oct. 1997;53(10):790-802.*
Lee et al. BACE overexpression alters the subcellular processing of APP and inhibits Abeta deposition in vivo. J Cell Biol. Jan. 17, 2005;168(2):291-302.*
Masliah et al. Comparison of neurodegenerative pathology in transgenic mice overexpressing V717F beta-amyloid precursor protein and Alzheimer's disease. J Neurosci. Sep. 15, 1996;16(18):5795-811.*
Chiocco et al., Soc. Neurosci, Abstr. No. 13647, p. 27 (2001).
Roberds et a., Hum. Mol. Genet., 10, pp. 1317-1324 (2001).
Luo et al., Nat. Neurosci., 3, pp. 231-232 (2001).
Cai et al., Nat. Neurosci., 4, pp. 233-234 (2001).
Cruts et al., Neurosci. Lett., 313, pp. 105-107 (2001).
Bodendorf et al., Soc. Neuosci., Abstr. No. 13445, p. 27 (2001).
Hsiao et al., Science, 274, pp. 99-102 (1996).
Vassar et al., Science, 286, pp. 735-741 (1999).
Kitaguchi et al., Nature, 331, pp. 530-532 (1988).
Tanzi et al., Nature, 331, pp. 528-530 (1988).
Tanzi et al., Nature, 329, pp. 156-157 (1987).
Games et al., Nature, 373, pp. 523-527 (1995).
Weidemann et al., Cell, 57, pp. 115-126 (1989).
Lichtenthaler et al., Biochemistry. 36, pp. 15396-15403 (1997).
Baumeister et al., Angew. Chem. Int. Ed., 37, pp. 2978-2982 (1998).
Yoshikai et al., Gene., 87, pp. 257-263 (1990).
Van Leuven, F., Progress in Neurobiology, 61, pp. 305-312 (2000).
Emilien et al., Arch. Neurol., 57, pp. 176-181 (2000).
Bodendorf U., et al., Journal of Neurochemistry, vol. 80, No. 5, pp. 799-806 (2002).

* cited by examiner

*Primary Examiner*—Daniel M. Sullivan
(74) *Attorney, Agent, or Firm*—George W. Johnston; Dennis P. Tramaloni; Brian C. Remy

(57) ABSTRACT

The present invention relates to a novel animal model for amyloidopathies, especially Alzheimer' disease overexpressing human BACE and human APP London. This novel animal model exhibits several aspects of amyloidopathy. The present invention also relates to a method for producing the double transgenic animals, to cells and cell lines derived from these animals and to a kit comprising these cells. Moreover, a method for the evaluation of the in vivo effects of beta-secretase activity on A-beta peptide generation, amyloidosis, neurodegeneration and AD pathology in these animals is provided.

9 Claims, 20 Drawing Sheets
(10 of 20 Drawing Sheet(s) Filed in Color)

Map of the APP transgenic constructs

AD124 Construct.

A

| Construct | founder | Tg nb | SB Tg copies | RT-PCR GAPDH | normalized | NB % of actin | | WB | |
|---|---|---|---|---|---|---|---|---|---|
| Prp-Asp2 | M5 | 0 | | | | | | | |
| | F10 | 5 | 5 | 9 | 8.8 | 40 | 56 | *** | *** |
| | M12 | 21 | 1 | 12.5 | 11.5 | 25 | 17 | - | - |
| | M13 | 23 | 10-20 | 7.5 | 7.4 | 111 | 109 | ***(*) | **** |
| | M15 | 18 | 1 | 8 | 8.8 | 24 | 34 | **(*) | *(*) |
| | F17 | 12 | 1 | 9.7 | 9.8 | 34 | 38 | ** | - |
| | M24 | 23 | 5-10 | 9 | 7.8 | 199 | 212 | **** | **** |
| | M34 | 0 | | | | | | | |
| | M37 | 18 | 1 | 11 | 11 | 9 | 12 | (*) | - |
| | M38 | 9 | 1-2 | 8 | 8.8 | 71 | 96 | *** | *** |

| neg.cont | | | | 20.4 | 21.2 | 12.4 | 1.2 | - | - |
|---|---|---|---|---|---|---|---|---|---|
| neg.cont | | | | 20.6 | 22.2 | 16.8 | 16.9 | - | - |

B

A

B

DOUBLE TRANSGENIC MICE OVEREXRESSING HUMAN BETA SECRETASE AND HUMAN APP-LONDON

BACKGROUND OF THE INVENTION

The present invention relates to novel double transgenic non-human animals useful to model diseases involving amyloidopathies, in particular Alzheimer's disease. Such transgenic animals will have utility in developping specific and general therapies for the treatment of amyloidopathies and in screening methods to identify novel anti-amyloidogenic compounds. The present invention is further directed to a method for the generation of such transgenic animals, to the evaluation of the in vivo effects of beta-secretase activity on amyloid peptide generation, amyloidosis, neurodegeneration and Alzheimer's pathology through the use of such novel transgenic animals.

Alzheimer's disease (AD) is a neurodegenerative disease which is characterized by memory loss and decline of cognitive functions (McKhann G, Drachman D, Folstein M, Katzman R, Price D, Stadlan E M. Clinical diagnosis of Alzheimer's disease: report of the NINCDS-ADRDA Work Group under the auspices of Department of Health and Human Services Task Force on Alzheimer's Disease. Neurology. 1984.34:939–44). The prevalence of AD approximately doubles with every five years over the age of 65. Overall, approximately 5 to 10% of those over 65 are affected (Scorer C A. Preclinical and clinical challenges in the development of disease-modifying therapies for Alzheimer's disease. DDT. 2001.6: 1207–1219). The clinical diagnosis of AD remains an exclusion diagnosis. Only post-mortem microscopic examination of the brain offers a definitive diagnosis based on the presence of extracellular plaques containing fibrils of amyloid-beta (A-beta) peptide and intracellular tangles containing polymerized phosphorylated Tau protein (Glenner G G, Wong C W. Alzheimer's disease and Down's syndrome: sharing of a unique cerebrovascular amyloid fibril protein. Biochem Biophys Res Commun. 1984. 22:1131–5; Spillantini M G, Goedert M, Jakes R, Klug A. Different configurational states of beta-amyloid and their distributions relative to plaques and tangles in Alzheimer disease. Proc Natl Acad Sci U S A. 1990. 87:3947–51). In most of the cases, AD occurs late in onset and sporadically. The early onset familial AD represents a minority of the cases, but they have been extremely important for the progression in the understanding of the disease mechanisms. Mutations in three genes have been shown to cause early-onset familial AD (FAD): Amyloid Precursor Protein (APP) (Chartier-Harlin M C, Crawford F, Houlden H, Warren A, Hughes D, Fidani L, Goate A, Rossor M, Roques P, Hardy J, et al. Early-onset Alzheimer's disease caused by mutations at codon 717 of the beta-amyloid precursor protein gene. Nature. 1991. 353: 844–6; Goate A, Chartier-Harlin M C, Mullan M, Brown J, Crawford F, Fidani L, Giuffra L, Haynes A, Irving N, James L, et al. Segregation of a missense mutation in the amyloid precursor protein gene with familial Alzheimer's disease. Nature. 1991.349:704–6; Murrell J, Farlow M, Ghetti B, Benson M D. A mutation in the amyloid precursor protein associated with hereditary Alzheimer's disease. Science. 1991. 254: 7–9; Mullan M, Houlden H, Windelspecht M, Fidani L, Lombardi C, Diaz P, Rossor M, Crook R, Hardy J, Duff K, et al. A locus for familial early-onset Alzheimer's disease on the long arm of chromosome 14, proximal to the alpha 1-antichymotrypsin gene. Nat Genet. 1992. 2: 340–2), PresenilinI (PsenI) (Sherrington R, Rogaev E I, Liang Y, Rogaeva E A, Levesque G, Ikeda M, Chi H, Lin C, Li G, Holman K, et al. Cloning of a gene bearing missense mutations in early-onset familial Alzheimer's disease. Nature. 1995. 375:754–60), and Presenilin 2 (Psen2) (Levy-Lahad E, Wijsman E M, Nemens E, Anderson L, Goddard K A, Weber J L, Bird T D, Schellenberg G D. A familial Alzheimer's disease locus on chromosome 1. Science. 1995. 269:970–3). Known missense mutations affect codon 717 of APP (altering V717*1, V717+G and V717+F in the polypeptide), while codons 670/671 (altering K670+N and M671+L in the polypeptide, hereinafter referred to as the Swedish mutation) are altered in the APP gene of a Swedish AD pedigree (numbers according to APP770). All these mutations affect the proteolytic processing of APP yielding more amyloidogenic peptides. APP can be processed by at least 3 secretases: alpha-, beta-, and gamma-secretases. Beta-secretase initiates A-beta peptide generation by cleaving APP after Methionine 671 (APP770 numbering) leading to a 12 kd retained membrane carboxyterminal fragment (Citron M, Teplow D B, Selkoe D J. Generation of amyloid beta protein from its precursor is sequence specific. Neuron. 1995. 14:661–70). The 12 kd fragment may then undergo gamma-secretase cleavage within the hydrophobic transmembrane domain to release the 40, 42, or 43 residue A-beta peptides (Seubert P, Vigo-Pelfrey C, Esch F, Lee M, Dovey H, Davis D, Sinha S, Schlossmacher M, Whaley J, Swindlehurst C. Isolation and quantification of soluble Alzheimer's beta-peptide from biological fluids. Nature. 1992.359: 325–7).

Current treatments for AD provide only modest symptomatic relief. There is a real need for disease modifying agents that slow the course of the disease and prevent or delay the disease in susceptible individuals. The development of such agents requires, among others, progress in the understanding of the molecular basis of the disease and in the development of animal models.

The strategies used to reproduce the disease in animal models mainly reflects the divergent causes of AD: aging, APP and Psen FAD mutations.

A number of transgenic mouse lines overexpressing either human wildtype APP, or human APP with FAD mutations at the beta-secretase cleavage site (APP Swedish mutant; Hsiao K, Chapman P, Nilsen S, Eckman C, Harigaya Y, Younkin S, Yang F, Cole G. Correlative memory deficits, Abeta elevation, and amyloid plaques in transgenic mice. Science. 1996. 274:99–102) and/or at the gamma-secretase cleavage site (APP London mutant; Games D, Adams D, Alessandrini R, Barbour R, Berthelette P, Blackwell C, Carr T, Clemens J, Donaldson T, Gillespie F. Alzheimer-type neuropathology in transgenic mice overexpressing V717F beta-amyloid precursor protein. Nature. 1995. 373:523–27) have been generated. These transgenic mouse lines have been crossed with transgenic lines overexpressing human Psen1 or Psen2 (gamma secretase activity) FAD mutants. Double transgenic mice show increased amyloid load but do not recapitulate all the aspects of the disease (for review see Van Leuven F. Single and multiple transgenic mice as models for Alzheimer's Disease. Progress in Neurobiology. 2000. 61, 305–312; Emilien G, Maloteaux J. M, Beyreuther K, and Masters C. L. Alzheimer Disease. Mouse models pave the way for therapeutic opportunities. Arch. Neurol. 2001. 57, 176).

Despite the fact that no FAD has up to now, been associated with mutation in human BACE (beta secretase activity) (Cruts M, Dermaut B, Rademakers R, Roks G, Van den Broeck M, Munteanu G, van Duij C M, Van Broeckhoven C. Amyloid beta secretase gene (BACE) is neither mutated in nor associated with early-onset Alzheimer's disease. Neurosci Lett. 2001. 313:105–7), BACE remains an attractive key player in the AD pathology. As a matter of fact, mice deficient in BACE (Cai H, Wang Y, Mc Carthy D, Wen H, Borchelt D. R, Price D. L, and Wong P. C. BACE1 is the major beta-secretase for generation of A-beta peptides by neurons. Nat. Neuroscience 2001. 4, 233; Luo Y, Bolon B, Kahn S, Bennett B D, Babu-Khan S, Denis P, Fan W, Kha H, Zhang J, Gong Y, Martin L, Louis J C, Yan Q, Richards W G, Citron M, Vassar R. Mice deficient in BACE1, the Alzheimer's beta-secretase, have normal phenotype and abolished beta-amyloid generation. Nat Neurosci. 2001. 3:231–2; Roberds SL, Anderson J, Basi G, Bienkowski M J, Branstetter D G, Chen K S, Freedman S B, Frigon N L, Games D, Hu K, Johnson-Wood K, Kappenman K E, Kawabe T T, Kola I, Kuehn R, Lee M, Liu W, Motter R, Nichols N F, Power M, Robertson D W, Schenk D, Schoor M, Shopp G M, Shuck M E, Sinha S, Svensson K A, Tatsuno G, Tintrup H, Wijsman J, Wright S, McConlogue L. BACE knockout mice are healthy despite lacking the primary beta-secretase activity in brain: implications for Alzheimer's disease therapeutics. Hum Mol Genet. 2001. 10:1317–24) have been shown to lack A-beta peptides in the brain demonstrating the absolute need of BACE for the cleavage of APP. These findings also increase the validity of BACE as a drug target for AD.

Recently mice overexpressing human APP with FAD mutation at the beta-secretase site (APP Swedish) and overexpressing human BACE (beta secretase activity) have been reported (Chiocco M J and Lamb B T. Generation and characterization of genomic-based beta-secretase transgenic mice. Soc. Neurosci. Abstr. No. 13647. 2001. 27; Bodendorf U, Sturchler-Pierrat C, Christnacher A, Sommer B, Staufenbiel M, and Paganetti P. Mice transgenic for human BACE show increased beta-secretase activity in vivo. Soc. Neurosci. Abstr. No. 13445. 2001. 27).

The overexpression of BACE together with APP Swedish is redundant in the sense that both proteins target the same metabolic step of APP. As a matter of fact, it has been shown that BACE overexpression results in increased beta-secretase cleavage of both wild-type APP and Swedish APP but increased secretion of amyloid peptides is only observed with the wild-type, but not with the Swedish APP suggesting that gamma-secretase level is inadequate to process the amount of C99 fragment produced in case of APP Swedish mutant (Vassar R, Bennett B D, Babu-Khan S, Kahn S, Mendiaz E A, Denis P, Teplow D B, Ross S, Amarante P, LoelofR, Luo Y, Fisher S, Fuller J, Edenson S, Lile J, Jarosinski M A, Biere A L, Curran E, Burgess T, Louis J C, Collins F, Treanor J, Rogers G, Citron M. Beta-secretase cleavage of Alzheimer's amyloid precursor protein by the transmembrane aspartic protease BACE. Science. Oct. 22, 1999;286(5440):735–41).

OBJECTS AND SUMMARY OF THE INVENTION

The above-defined technical problem is solved by the present invention which provides a novel animal model comprising the association of human APP with FAD mutation at the gamma-secretase cleavage site and human BACE (beta secretase activity) resulting in increased cleavage at both the beta-secretase and gamma-secretase sites of APP which correspond to N- and C-termini of amyloid peptides, respectively. In addition, mutations in the transmembrane domain of APP have been shown to alter gamma-secretase activity in favour of A-beta peptide 42 (Lichtenthaler S F, Ida N, Multhaup G, Masters C L, Beyreuther K. Mutations in the transmembrane domain of APP altering gamma-secretase specificity. Biochemistry. 1997 Dec. 9;36(49): 15396–403). The present invention should thus favour the production of amyloid peptide species A-beta 42 which is described as the most pathogenic form of A-beta (Baumeister R, Eimer S. Amyloid aggregates, presenilins, and Alzheimer's disease. Angew. Chem. Int. Ed. 1998. 37(21):2978–2982).

The present invention relates to novel double transgenic non-human animals useful to model diseases involving amyloidopathies, in particular Alzheimer's disease. More particularly the invention relates to an animal model involving transgenic manipulation of amyloid precursor protein (APP) and beta-secretase (BACE). Transgenic mice were generated overexpressing human BACE and human APP London. Such transgenic animals will have utility in developing specific and general therapies for the treatment of amyloidopathies and in screening methods to identify novel anti-amyloidogenic compounds. The present invention is further directed to a method for the generation of such transgenic animals, to cells derived from such animals as well as to a kit comprising these cells for screening of compounds useful in the treatment of amyloidopathies, and to the evaluation of the in vivo effects of beta-secretase activity on A-beta generation, amyloidosis, neurodegeneration and AD pathology through the use of such novel transgenic animals.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
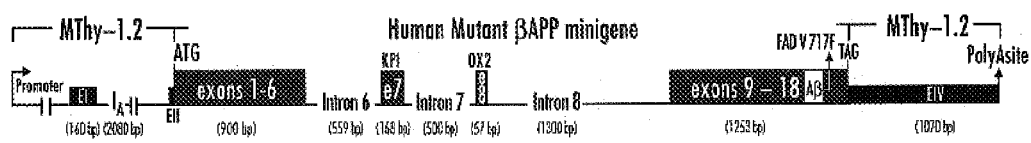
FIG. 1. Schematic diagram showing AD 124 (11.5-kbp) construct which was used to generate transgenic mice.

The present invention provides a novel non-human animal model, such as mice, to model neurodegenerative diseases involving amyloidopathies, in particular, AD. More particularly, the present invention provides a transgenic non-human animal whose genome incorporates DNA comprising a coding sequence which encodes the human APP London operably linked to a regulatory sequence and a coding sequence encoding the human beta-secretase operably linked to a regulatory sequence.

As used herein, "beta-secretase" is defined as an aspartyl-protease generating the N-terminus of A-beta. Preferred beta-secretases are human BACE and BACE-2. Most preferred is human BACE with the amino acid sequence as disclosed in SEQ ID NO:9. The BACE amino acid sequence of SEQ ID NO:9 may be encoded by the nucleotide sequence as disclosed in SEQ ID NO:8. The beta-secretase can be a full-length beta-secretase or a truncated beta-secretase at least exhibiting the active site. Preferably, beta-secretase is a full-length beta-secretase. Beta-secretases may contain amino acid substitutions if such substitutions do not generally alter the beta-secretase activity. Amino acid substitutions in proteins and polypeptides which do not essentially alter biological activity are known in the art and are described by H. Neurath and R. L. Hill in "The Proteins", Academic Press, New York (1979). Six general classes of amino acid side chains, categorized as described above, include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). Beta-secretases can additionally contain sequences of several amino acids which are encoded for by "linker" sequences. These sequences arise as a result from the expression vectors used for recombinant expression of beta-secretases. Beta-secretases of the present invention can also contain specific sequences attached to the N-terminus that are signal sequences.

A number of cDNA forms of APP have been identified, encoding among others the three most abundant isoforms APP695, APP751, and APP770. These forms arise from a single precursor RNA by alternate splicing. The gene spans more than 175 kb with 18 exons (Yoshikai S, Sasaki H, Doh-ura K, Furuya H, Sakaki Y. Genomic organization of the human amyloid beta-protein precursor gene. Gene. 1990. 87(2):257–63). APP contains an extracellular domain, a transmembrane region and a cytoplasmic domain. A-beta consists of up to 28 amino acids just outside the hydrophobic transmembrane domain and up to 15 residues of this transmembrane domain. Thus, A-beta is a cleavage product derived from APP which is normally found in brain and other tissues such as heart, kidney and spleen. However, A-beta deposits are usually found in abundance only in the brain. The larger alternate forms of APP (APP751, APP770) consist of APP695 plus one or two additional domains. APP751 consists of all 695 amino acids of APP695 plus an additional 56 amino acids which has homology to the Kunitz family of serine protease inhibitors (KPI) (Tanzi R E, McClatchey A I, Lamperti E D, Villa-Komaroff L, Gusella J F, Neve R L. Protease inhibitor domain encoded by an amyloid protein precursor mRNA associated with Alzheimer's disease. Nature. 1988. 331:528–30; Weidemann A, Konig G, Bunke D, Fischer P, Salbaum J M, Masters C L, Beyreuther K. Identification, biogenesis, and localization of precursors of Alzheimer's disease A4 amyloid protein. Cell. 1989 Apr. 7;57(1):115–26. Kitaguchi N, Takahashi Y, Tokushima Y, Shiojiri S, Ito H. Novel precursor of Alzheimer's disease amyloid protein shows protease inhibitory activity. Nature. 1988 Feb. 11; 331(6156):530–2.; Tanzi R E, St George-Hyslop P H, Haines J L, Polinsky R J, Nee L, Foncin J F, Neve R L, McClatchey A I, Conneally P M, Gusella J F. The genetic defect in familial Alzheimer's disease is not tightly linked to the amyloid beta-protein gene. Nature. 1987. 329 (6135):156–7). APP770 contains all 751 amino acids of APP751 and an additional 19 amino acid domain homologous to the neuron cell surface antigen OX-2 (Weidemann et al. 1989; Kitaguchi et al. 1988). Unless otherwise noted, the amino acid positions referred to herein are the positions as they appear in APP770. The amino acid number of equivalent positions in APP695 and APP751 differ in some cases due to the absence of the OX-2 and KPI domains. By convention, the amino acid positions of all forms of APP are referenced by the equivalent positions in the APP770 form. Unless otherwise noted, this convention is followed herein. Unless otherwise noted, all forms of APP and fragments of APP, including all forms of A-beta, referred to herein are based on the human APP amino acid sequence. APP is post-translationally modified by the removal of the leader sequence and by the addition of sulfate and sugar groups.

As used herein, "APP London" (AppLo) is defined as an APP isoform as defined above containing one or more of the either natural or artificial mutations which affect the production of amyloid peptides towards a specific increased production of A-beta 42 peptide. Preferred are natural APP mutations around the gamma-secretase cleavage site with pathological relevance including T714I (Kumar-Singh S, De Jonghe C, Cruts M, Kleinert R, Wang R, Mercken M, De Strooper B, Vanderstichele H, Lofgren A, Vanderhoeven I, Backhovens H, Vanmechelen E, Kroisel P M, Van Broeckhoven C. Non-fibrillar diffuse amyloid deposition due to a gamma (42)-secretase site mutation points to an essential role for N-truncated A beta(42) in Alzheimer's disease. Hum Mol Genet. 2000 Nov. 1;9(18):2589–98.)

V715M (Ancolio K, Dumanchin C, Barelli H, Warter J M, Brice A, Campion D, Frebourg T, Checler F. Unusual phenotypic alteration of beta amyloid precursor protein (betaAPP) maturation by a new Val-715-->Met betaAPP-770 mutation responsible for probable early-onset Alzheimer's disease. Proc Natl Acad Sci U S A. 1999 Mar. 30;96(7):4119–24.)

I716V (Eckman C B, Mehta N D, Crook R, Perez-tur J, Prihar G, Pfeiffer E, Graff-Radford N, Hinder P, Yager D, Zenk B, Refolo L M, Prada C M, Younkin S G, Hutton M, Hardy J. A new pathogenic mutation in the APP gene (I716V) increases the relative proportion of A beta 42(43). Hum Mol Genet. 1997 November; 6(12):2087–9.)

V717F (Murrell J, Farlow M, Ghetti B, Benson M D. A mutation in the amyloid precursor protein associated with hereditary Alzheimer's disease. Science. 1991 Oct. 4;254(5028):97–9.)

V717G (Chartier-Harlin M C, Crawford F, Houlden H, Warren A, Hughes D, Fidani L, Goate A, Rossor M, Roques P, Hardy J, et al. Early-onset Alzheimer's disease caused by mutations at codon 717 of the beta-amyloid precursor protein gene. Nature. 1991 Oct. 31; 353(6347):844–6.)

V717I (Goate A, Chartier-Harlin M C, Mullan M, Brown J, Crawford F, Fidani L, Giuffra L, Haynes A, Irving N, James L, et al. Segregation of a missense mutation in the amyloid precursor protein gene with familial Alzheimer's disease. Nature. 1991 Feb. 21;349(6311):704–6)

V717L (Murrell J R, Hake A M, Quaid K A, Farlow M R, Ghetti B. Early-onset Alzheimer disease caused by a new mutation (V717L) in the amyloid precursor protein gene. Arch Neurol. 2000 June; 57(6):885–7.)

L723P (Kwok J B, Li Q X, Hallupp M, Whyte S, Ames D, Beyreuther K, Masters C L, Schofield P R. Novel Leu723Pro amyloid precursor protein mutation increases amyloid beta42(43) peptide levels and induces apoptosis. Ann Neurol. 2000 February; 47(2): 249–53.) Preferred are also artificial mutations (replacement of all residues in the transmembrane region outside of the A-beta domain) examples of which and their consequence on the gamma-secretase cleavage have been described by Lichtenthaler and co-workers (Lichtenthaler S F, Wang R, Grimm H, Uljon S N, Masters C L, Beyreuther K. Mechanism of the cleavage specificity of Alzheimer's disease gamma-secretase identified by phenylalanine-scanning mutagenesis of the transmembrane domain of the amyloid precursor protein. Proc Natl Acad Sci U S A. 1991 Mar. 16;96 (6):3053–8).

More preferred is human APP London containing the natural V717F mutation. Most preferred is human APP London encoded by SEQ ID NO:1 (AppLo).

Degenerative brain condition is defined as one or several of the following parameters: neuronal cell death, neuronal cell loss, dystrophic neurites, synaptic disappearance, increase of oxidative damage intermediates such as 3-nitrotyrosine and 4-hydroxy-2-nonenal, presence of inflammatory markers. Examples of degenerative brain conditions include Alzheimer's disease.

Amyloidopathies are diseases characterized by the accumulation of amyloid in tissues. Examples of amyloidopathies include Alzheimer's disease (AD), Down's syndrome (DS), familial British dementia (FBD), familial amyloidotic polyneuropathy (FAP), and Gerstmann-Sträussler syndrome (GSS).

Figure 6:
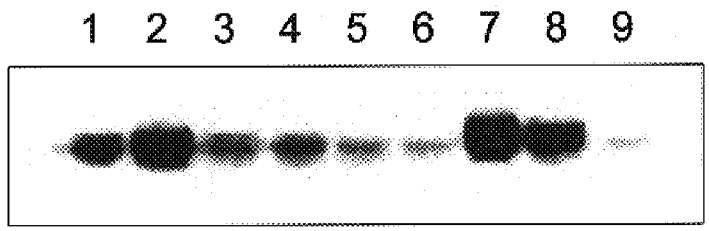
FIG. 6: Panel A: Comparative table showing the results obtained for the different BACE lines in Southern blot (SB), Northern blot (NB), Kinetic PCR (RT-PCR) and Western blot (WB) analysis. For SB, 3 to 4 mice per line were analyzed and an estimation of the mean value is represented. For RT-PCR, NB and WB, the individual values of the 2 mice analyzed are shown. Note that for the normalized results of the RT-PCR the lower the value, the higher the level of mRNA. Panel B: Western blot analysis of BACE transgenic lines with mAb BSC-1; 1: line 10; 2: line 13; 3 and 4: line 15; 5 and 6: line 17; 7: line 24; 8: line 38; 9: negative line.

More specifically, the present invention relates to a transgenic non-human animal model, expressing human APP London at levels higher than endogenous APP (FIG. 9) and expressing human BACE at levels higher than the amount of endogenous BACE (FIG. 6).

Moreover, the present invention relates to a double transgenic animal model overexpressing human BACE and human APP London ([BACE×APP London] double transgenic mice; hBACE/hAPPLo) which develops with age amyloid plaques and amyloid deposits in the vessels (FIG. 10).

More specifically, the present invention relates to a double transgenic animal model overexpressing human BACE and human APP London where congophilic staining can be detected at the age of 11 months.

It is a further object of the present invention to provide transgenic animals exhibiting one or more histopathologies similar to those of AD, which include extracellular A-beta deposition, tangles, phosphorylated Tau protein, inflammatory response (astrocytosis, microgliosis), dystrophic neuritic components, loss of synaptic density, and cytoskeletal alterations with regional specificity resembling that of AD.

The transgenic non-human animals of the present invention are preferably mammals. More preferably, the animals are rodents. Most preferably, the animals are mice. The present invention also relates to descendants of the transgenic non-human animals, obtained by breeding with the same or with another phenotype.

The present invention further provides a cell line or primary cell culture as well as an organotypic brain slice culture derived from the transgenic non-human animal or its descendants.

A further objective of the present invention is the use of the transgenic non-human animal or a cell line or an organotypic brain slice culture as a model for amyloidopathies, especially as a model for AD.

More specifically, the transgenic non-human animal, or animal cells derived thereof, can be used to investigate the pathological course of AD and to screen for compounds preventing or altering the pathological course of AD as measured by their effect on the amount of APP cleavage products, neuropathology and behavioral alterations.

The present invention further provides a method of producing a transgenic non-human animal whose genome incorporates DNA comprising a coding sequence which encodes the human APP London operably linked to a regulatory promoter sequence and a coding sequence encoding human beta-secretase operably linked to a regulatory promoter sequence.

Transgenic mice are achieved routinely in the art using the technique of microinjection, as described in U.S. Pat. No. 4,736,866 issued to Leder et al., and as provided by B. Hogan et al. entitled "Manipulating the Mouse Embryo: A Laboratory Manual", Ed. 2, pp. 89–204. Plainview, N.Y.: Cold Spring Harbor Laboratory, USA (1995). Further methods for the production of a transgenic non-human animal, for example a transgenic mouse, comprise introduction of a targeting vector into a germ cell, an embryonic cell, stem cell or an egg or a cell derived therefrom.

For these studies, the constructs are introduced into animal embryos using standard techniques such as microinjection or embryonic stem cells. Cell culture based models can also be prepared by two methods. Cell cultures can be isolated from the transgenic animals or prepared from established cell cultures using the same constructs with standard cell transfection techniques.

More particularly, the method for producing double transgenic non-human animals whose genome incorporates DNA comprising a coding sequence which encodes the human APP London operably linked to a regulatory promoter sequence and a coding sequence encoding human beta-secretase operably linked to a regulatory promoter sequence comprises (a) introducing a DNA construct comprising a coding sequence which encodes human beta-secretase and a regulatory sequence which is operably linked to the coding sequence into a cell or embryo, (b) introducing a DNA construct comprising a coding sequence which encodes human APP London and a regulatory sequence which is operably linked to the coding sequence into a cell or embryo (c) generating a transgenic animal from each of the said cells or embryos (d) and crossbreeding the said transgenic animals.

According to the present invention, the method for producing double transgenic non-human animals might also comprise co-injecting the two different DNA constructs mentioned above (linked in the same vector construct or independent on two different vectors) into a single cell or embryo and generating a double transgenic animal.

One of the vector constructs used in the method of the present invention comprises a coding sequence which encodes human beta-secretase and a regulatory sequence which is operably linked to the coding sequence. Optionally, the coding sequence of human beta-secretase is interrupted by intron sequences of the human beta-secretase gene. The other vector construct used in the method of the present invention comprises a coding sequence which encodes the human APP containing a London mutation operably linked to a regulatory promoter sequence. Optionally, the coding sequence of human APP London is interrupted by intron sequences of the human APP gene. Preferably, the regulatory sequences direct the expression of the transgenes in brain tissue. Preferably, the regulatory sequence operably linked to the coding sequence of human beta-secretase is the prion promoter sequence. Most preferably, the prion promoter sequence is the mouse prion promoter sequence. Preferably, the regulatory sequence operably linked to the coding sequence of human APP containing the London mutation is the Thy-1 promoter sequence. Most preferably, the Thy-1 promoter sequence is the mouse Thy-1.2 promoter sequence.

However, other promoters may be used which may be selected for the following criteria:

high level of expression

Examples of promoters known to induce high transgene expression: beta actin promoter, platelet derived growth factor B (PDGF-B) chain gene promoter, metallothionein I promoter, elongation factor 1-alpha promoter, prion protein promoter, Thy-1 promoter, RNA polymerase I promoter, RNA polymerase II promoter brain-specific expression Examples of promoters known to induce specific expression in cells present in the brain: metallothionein III promoter, neuron specific enolase (NSE) promoter, sodium channel promoter, neurofilament M (NF-M) promoter, neurofilament L (NF-L)promoter, neurofilament H (NF-H) promoter, glial fibrillary acidic protein (GFAP) promoter, myelin basic protein (MBP) promoter, Proteolipid protein (Plp) promoter, Tyrosine Hydroxylase (TH) promoter, aldolase C promoter, synapsin I promoter, rhombotin l promoter, dopamine beta hydroxylase (DBH) promoter, choline acetyltransferase (ChAT), Purkinje cell (Pcp2) promoter.

The constructs used may also employ an enhancer sequence. Enhancers may be used which may be selected from the following: immunoglobulin kappa 3'-enhancer, lambda enhancer, IgH 3'-enhancer, T cell receptor alpha enhancer, alpha HS-26 enhancer, alpha HS-40 enhancer, SV40 enhancer and rat insulin II gene enhancer.

Other elements in vector constructs may be included such as
  intronic sequences between promoter and coding sequence or 3' of the coding sequence. Their role is to increase the stability of the transcript.
  poly A signal which can originate from a locus different from the locus from which the promoter originates. Examples of poly A signals commonly used: huGH, SV40.
  specific DNA sequences placed 5' and/or 3' of the [promoter-coding sequence] construct. The role of those sequences is to favour an open conformation of the chromatin thus increasing the probability of transcription. Examples of such sequences are: Dominant control regions (DCR) as identified in the beta-globin locus (Talbot D, Collis P, Antoniou M, Vidal M, Grosveld F, Greaves D R. A dominant control region from the human beta-globin locus conferring integration site-independent gene expression. Nature. 1998 Mar. 23;338(6213):352–5.); Matrix attachment regions (MAR) as identified in the lysozyme locus (Phi-Van L, von Kries J P, Ostertag W, Stratling W H. The chicken lysozyme 5' matrix attachment region increases transcription from a heterologous promoter in heterologous cells and dampens position effects on the expression of transfected genes. Mol Cell Biol. 1990 May; 10(5): 2302–7., McKnight R A, Shamay A, Sankaran L, Wall R J, Hennighausen L. Matrix-attachment regions can impart position-independent regulation of a tissue-specific gene in transgenic mice. Proc Natl Acad Sci U S A. 1992 Aug. 12;89(15):6943–7.); DNA hypersensitive sites (DHSS) as identified in the metallothionein locus (Palmiter R D, Sandgren E P, Koeller D M, Brinster R L. Distal regulatory elements from the mouse metallothionein locus stimulate gene expression in transgenic mice. Mol Cell Biol. 1993 September;13(9): 5266–75.), Alu sequences as defined in the keratin 18 locus (Thorey I S, Cecena G, Reynolds W, Oshima R G. Alu sequence involvement in transcriptional insulation of the keratin 18 gene in transgenic mice. Mol Cell Biol. 1993 November; 13(11):6742–51).

Integration of the transgene can be detected by various methods comprising genomic southern blot and PCR analysis of 5' and 3' regions using DNA isolated from tail biopsies of two- to three-weeks old mice.

It will be apparent to the person skilled in the art that there are a large number of analytical procedures which may be used to detect the expression of the transgene comprising methods at the RNA level comprising mRNA quantification by reverse transcriptase polymerase chain reaction (RT-PCR) or by Northern blot, in situ hybridization, as well as methods at the protein level comprising histochemistry, immunoblot analysis and in vitro binding studies. Quantification of the expression levels of the transgenes can moreover be determined by the ELISA technology which is common to those knowledgeable in the art.

Quantitative measurement can be accomplished using many standard assays. For example, transcript levels can be measured using RT-PCR and hybridization methods including Rnase protection, Northern blot analysis, and RNA dot analysis. APP and A-beta levels can be assayed by ELISA, Western blot analysis, and by comparison of immunohistochemically stained tissue sections. Immunohistochemical staining as well as immuno-electron microscopy can also be used to assay localization of APP and A-beta to particular tissues and cell types. Specific examples of such assays are provided below.

"Polynucleotide" and "nucleic acid" refer to single or double-stranded molecules which may be DNA, comprised of the nucleotide bases A, T, C and G, or RNA, comprised of the bases A, U (substitutes for T), C, and G. The polynucleotide may represent a coding strand or its complement. Polynucleotide molecules may be identical in sequence to the sequence which is naturally occurring or may include alternative codons which encode the same amino acid as that which is found in the naturally occurring sequence (See, Lewin "Genes V" Oxford University Press Chapter 7, 1994, 171–174). Furthermore, polynucleotide molecules may include codons which represent conservative substitutions of amino acids as described. The polynucleotide may represent genomic DNA or cDNA.

The transgenic animals may be further characterized by investigating the neuropathology by methods known in the art comprising immunohistochemistry, electron microscopy, Magnetic Resonance Imaging (MRI) and by behavioral studies addressing neurological and cognitive functions. Examples of behavioral tests are: grip strength, wire manoeuvre, swim test, rotarod, locomotor activity, Morris water maze, Y-maze, light-dark preference, passive and active avoidance tests.

Furthermore, a method of screening test compounds for use in the treatment of a degenerative brain condition which method comprises administering a compound to a transgenic non-human animal of the invention and determining the effect of the compound on a disease marker comprising the amount of APP cleavage products, neuropathology, and behavioral alterations is provided by the present invention. The method of screening can also employ organotypic brain slice culture or cells derived from the transgenic animals which method comprises administering the test compound to organotypic brain slice culture or to cells derived from the transgenic animal and determining the effect of the test compound on a disease marker comprising the amount of APP cleavage products.

The above-described method can also be used for screening test compounds for use in the prevention of a degenerative brain condition, therefore the present invention provides a method of screening test compounds for use in the prevention of a degenerative brain condition which method comprises administering a compound to a transgenic non-human animal of the invention and determining the effect of the compound on a disease marker comprising the amount of APP cleavage products, neuropathology, and behavioral alterations.

In another embodiment, a method for testing compounds for an effect on an AD marker which method comprises administering the compound to an animal and determining the effect of the compound on a disease marker is provided.

APP forms are preferred markers for assays to assess the potential for compounds to affect Alzheimer's disease. The absolute level of APP and APP transcripts, the relative levels of the different APP forms and their cleavage products, and localization of APP expression or processing are all markers associated with Alzheimer's disease that can be used to measure the effect of treatment with potential therapeutic compounds. The amount and localization of APP cleavage products to plaques and neuritic tissue is an especially preferred target for these assays.

In yet another embodiment, a method for testing the efficacy of a treatment for a degenerative brain condition associated with an overexpression of A-beta comprising exposing a transgenic animal to that treatment and determining the effect of the treatment on the amount and the localization of APP cleavage products, neuropathology and behavioral alterations is provided.

A method for the evaluation of the in vivo effects of beta-secretase activity on A-beta peptide generation, amyloidosis, neurodegeneration and AD pathology is also provided comprising measuring A-beta peptide, carrying out immunohistochemistry and electron microscopy of brain slices, and behavioral studies in the transgenic non-human animals of the invention. In a further embodiment, the disease markers are compared to a control animal. The control animal may be an animal which does not comprise a transgene for beta-secretase in its genome, and/or an animal which does not comprise any transgene in its genome.

Moreover, the invention provides a kit for screening compounds useful in the treatment of a degenerative brain condition including AD comprising a cell line or primary cell culture derived from a transgenic non-human animal of the invention and a means for determining whether a test compound inhibits the effects associated with overexpression of transgenes in said cell. The kit may also be used to screen for compounds useful in the prevention of a degenerative brain condition, including AD.

As used herein, "test compound" is intended to mean any compound which is being screened for preventing, inhibiting or reversing degenerative brain condition e.g. AD using the transgenic animals as well as organotypic brain slice cultures or cells derived thereof described herein. It is also understood that a "test compound", which is active in preventing, inhibiting or reversing AD, can subsequently be used in pharmaceutical compositions for the treatment of degenerative brain conditions involving A-beta production, preferably for the treatment of AD.

The compounds which can be tested and identified according to a method of the invention may be expression libraries, e.g., cDNA expression libraries, peptides, proteins, nucleic acids, antibodies, small organic compounds, hormones, peptidomimetics, PNAs or the like (Milner J. DNA damage, p53 and anticancer therapies. Nat Med. 1995. 1:879–880; Hupp TR. Small peptides activate the latent sequence-specific DNA binding function of p53. Cell. 1995.83:237–245; Gibbs JB, Oliff A. Pharmaceutical research in molecular oncology. Cell. 1994 Oct. 21;79(2): 193–8.).

The compounds isolated by the above methods can also serve as lead compounds for the development of analog compounds. Identification of analog compounds can be performed through use of techniques such as self-consistent field (SCF) analysis, configuration interaction (CI) analysis, and normal mode dynamics analysis. Computer programs for implementing these techniques are available; e.g., Rein, Computer-Assisted Modeling of Receptor-Ligand Interactions (Alan Liss, New York, 1989). Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Furthermore, said derivatives and analogues can be tested for their effects according to methods known in the art; see also supra. Furthermore, peptidomimetics and/or computer aided design of appropriate derivatives and analogues can be used, for example, according to the methods described above. Methods for the lead generation in drug discovery also include using proteins and detection methods such as mass spectrometry (Cheng et al. J. Am. Chem. Soc. 1995. 117:8859–60) and some nuclear magnetic resonance (NMR) methods (Fejzo et al., Chem. Biol. 1999. 6:755–69; Lin et al., J. Org. Chem. 1997. 62:8930–8931).

In a further embodiment, the invention provides a pharmaceutical composition comprising a test compound identified by the screening method of the present invention and a pharmaceutically acceptable carrier.

The present invention further provides a pharmaceutical composition comprising a test compound identified by a screening method of the present invention for use in the treatment of degenerative brain conditions including AD and a pharmaceutically acceptable carrier.

In accordance with this, the present invention also relates to a method of producing a drug comprising the steps of (I) synthesizing the test compound identified as useful in the treatment of a degenerative brain condition or an analog or derivative thereof in an amount sufficient to provide said drug in a therapeutically effective amount to a subject; and/or (ii) combining the test compound identified as useful in the treatment of a degenerative brain condition or an analog or derivative thereof with a pharmaceutically acceptable carrier.

Furthermore, the present invention relates to a method of producing a pharmaceutical composition comprising a screening method of the invention, modifying the identified compound and formulating the compound obtained with a pharmaceutically acceptable carrier.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, benzenesulfonic, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17$^{th}$ ed., Mack Publishing Company, Easton, Pa., 1985, p. 1418, the disclosure of which is hereby incorporated by reference.

The invention further provides the use of a test compound identified by the screening method of the present invention for the treatment of a degenerative brain condition including AD.

Moreover, the use of a test compound identified by the screening method of the present invention for the preparation of a medicament for the treatment of a degenerative brain condition including AD is provided.

In a further embodiment, the use of a transgenic non-human animal of the invention or a cell line or primary cell culture or an organotypic brain slice culture derived thereof for the screening of compounds useful in the prevention or treatment of degenerative brain diseases, is provided.

Having now generally described this invention, the same will become better understood by reference to the specific examples, which are included herein for purpose of illustration only and are not intended to be limiting unless otherwise specified, in connection with the following figures.

EXAMPLES

Commercially available reagents referred to in the examples were used according to manufacturer's instructions unless otherwise indicated.

Example 1

APPV717F Transgenic Mice

Transgenic mouse lines express human APP with the London mutation (V717F) under the control of the mouse Thy1 promoter (Malherbe P, Richards J. G, Bluethmann H, Martin J. R, Bleuel Z, Thomas, B, Fischer C, Diener C and Huber G. Transgenic mice overexpressing three isoforms of human mutant amyloid precursor protein driven by the neuron-specific elements of the thy-1 gene promoter. Soc. Neurosci., 1997. Abstr.23, 1636). These mouse lines were denominated AD124.

A. Generation of the Human APP London Vector Contruct

The London familial AD mutation (FAD, V717F substitution) was introduced in human βAPP$_{695}$ cDNA by site-directed mutagenesis as described previously (Malherbe P, Richards J G, Martin J R, Bluethmann H, Maggio J, Huber G. Lack of beta-amyloidosis in transgenic mice expressing low levels of familial Alzheimer's disease missense mutations. Neurobiol Aging. 1996. 17:205–14). By site directed mutagenesis (SDM), a BamH1 site was introduced at the beginning of exon 6 (nucleotides 807 to 810) in the human βAPP$_{695}$ FAD (V717F) cDNA and in the 3.0-kbp mini-hAPP gene fragment containing the exons 6, 7, 8, 9 and their flanking regions (Yamada T, Goto I, Sakaki Y. Neuron-specific splicing of the Alzheimer amyloid precursor protein gene in a mini-gene system. Biochem Biophys Res Commun. 1993.195:442–8). The 477-bp BamH1(SDM)-Xho1 fragment in βAPP$_{695}$ FAD cDNA was then replaced with 2.83-kbp BamH1(SDM)-Xho1 fragment from mini-hAPP gene to give 4.74-kbp hβAPP-FAD(V717F) mini-gene (SEQ ID NO:1). The MThy-1.2-hβAPP-FAD-mini-gene construct was generated by insertion of the 4.74-kbp hβAPP-FAD(V717F) mini-gene fragment into the XhoI site of a expression vector containing mouse Thy-1.2 glycoprotein gene and promoter (Acc No: M12379). This expression vector has a 6.8 kbp NotI-fragment comprising mouse Thy-1.2 gene (Vidal M, Morris R, Grosveld F, Spanopoulou E. Tissue-specific control elements of the Thy-1 gene. EMBO J. 1990. 9:833–40) in which 1.5 kbp BanI-XhoI fragment located on exon 2 and exon 4 was replaced by the XhoI cloning site. The MThy-1.2-hβAPP-FAD mini-gene vector was digested with NotI, which releases 11.5-kbp MThy-1.2-hβAPP-FAD mini-gene fragment (termed, AD124) (FIG. 1).

B. Establishment of AD124 Transgenic Mice

Linear AD124 fragment was microinjected into the male pronuclei of B6D2F1 zygotes (Hogan B, Constantini F, Lacy E. 1995. Manipulating the mouse embryo: a laboratory manual, Ed 2 pp. 89–204. Plainview, N.Y.: Cold Spring Harbor Laboratory). After microinjection, zygotes were reimplanted into the oviducts of pseudopregnant B6CBAF1 females. Integration of the transgene was detected both by genomic southern blot and PCR analysis of 5' and 3' regions, using DNA isolated from tail biopsies of 2- to 3-weeks old mice. For the 5' region PCR detection, following primers (MThy-1.2 sense: SEQ ID NO:2, hβAPP antisense: SEQ ID NO:3 which generate 1100-bp PCR fragment) and for the 3' region PCR detection, following primers (hβAPP sense: SEQ ID NO:4, MThy-1.2 antisense: SEQ ID NO:5 which generate 932-bp PCR fragment) were used. PCR was performed at 95° C. (2 min) for one cycle and then at 92° C. (1 min), 56° C. (1 min), 72° C. (1 min) for 35 cycles. The final cycle had an extension time of 10 min. Several microinjection of the AD124 construct resulted in the generation of 13 positive transgenic founder mice (lines 3, 15, 27, 42, 54, 64, 67, 68, 82, 83, 85, 90 and 97). Transgene founders were crossed with wild-type C57BL/6 mice to establish heterozygous offspring.

C. Characterization of Transgenic Animals

1. In Situ Hybridization and Histochemistry

Figure 2:
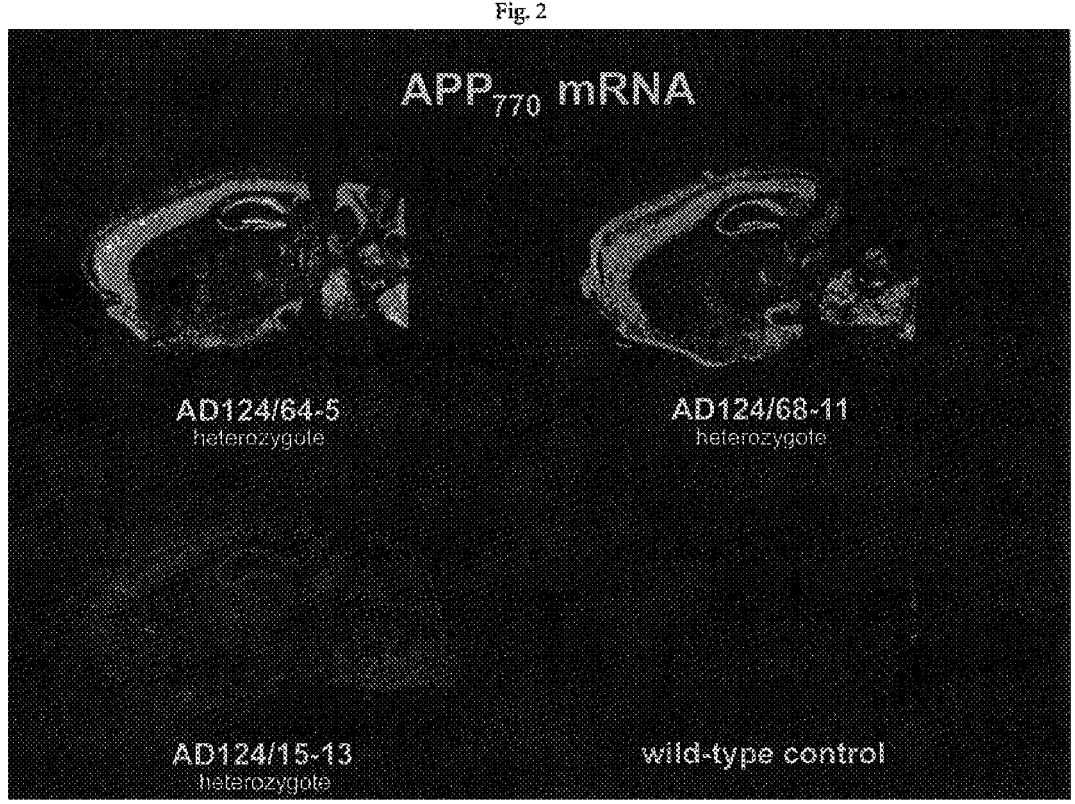
FIG. 2. Regional brain distribution of human βAPP$_{770}$ in AD124 transgenic and wild-type control mice using a 60-mer oligonucleotide probe, specific for the OX-2 domain (corresponding to amino acids 344–363 of human βAPP$_{770}$ (SEQ ID NO:6). Regions with high levels of transgene expression are colored white, green, yellow, red, or light blue and those with low levels are dark blue or grey to black. Note the high levels of expression in cerebral cortex and hippocampal formation in lines 64 and 68 and the much lower levels in the line 15 compared to a control.
Figure 3:
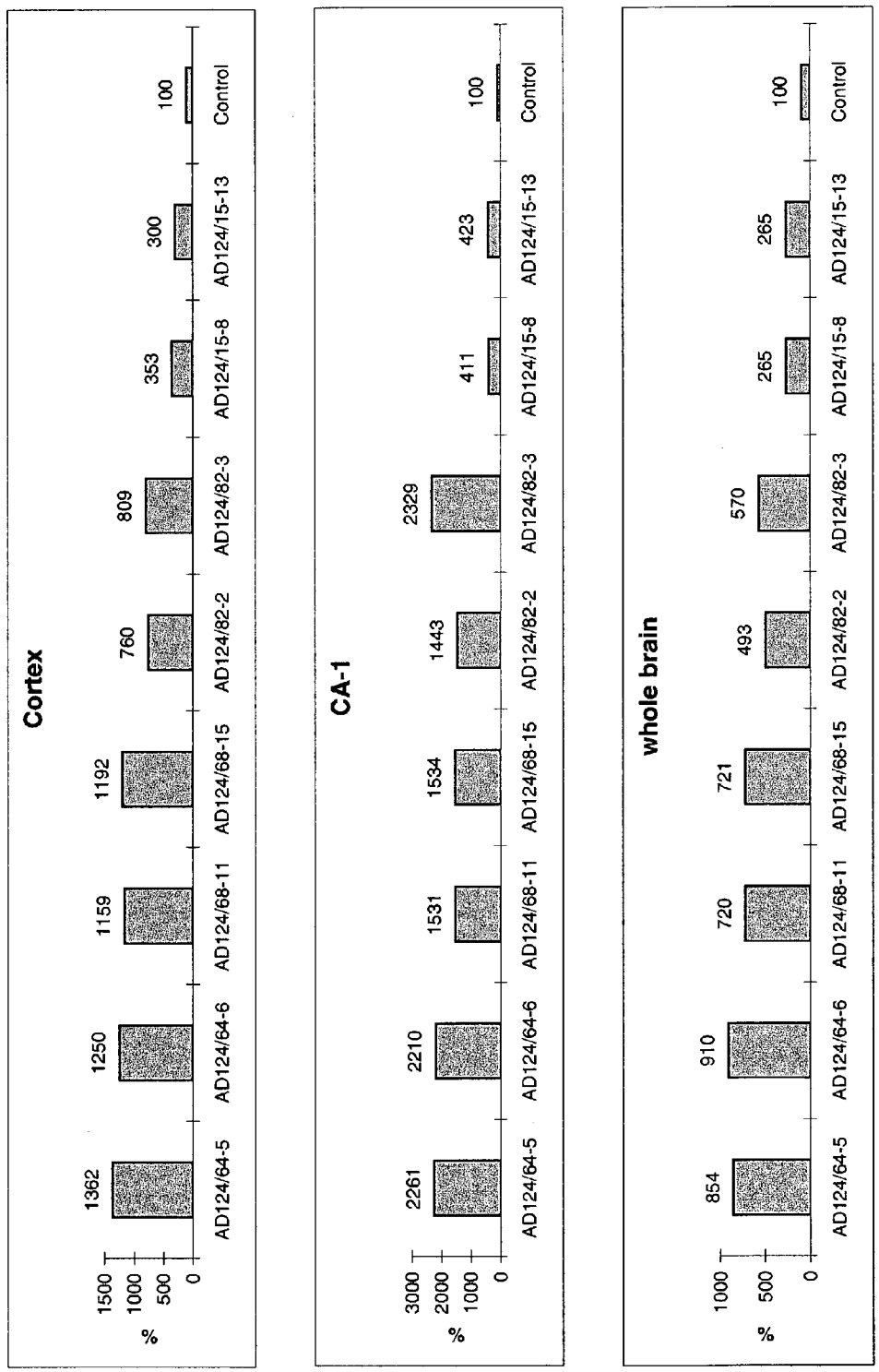
FIG. 3. Levels of βAPP$_{770}$ mRNA expression in AD 124 transgenic mice. Quantification of relative hybridization signal for human βAPP$_{770}$ in different lines of AD124 heterozygous mouse brains versus wild-type controls.

Halothane-anesthetized mice were decapitated, the brains removed and immediately frozen on dry ice then stored at −80° C. until used. Parasagittal cryostat sections (12 μm) of brain were mounted on slides, previously coated with 2% 3-aminopropyl-triethoxysilane in acetone, and then fixed in 4% paraformaldehyde (in phosphate-buffered saline, PBS, pH 7.4) for 20 min followed by three 5 min washing steps in PBS. 60-mer antisense polynucleotide probes specific for the OX-2 (hβAPP$_{770}$)(SEQ ID NO:6) and KPI (hβAPP$_{751+770}$)(Seq ID NO:7) domains (corresponding to amino acids 344–363 and amino acids 324–343 of human βAPP$_{770}$, respectively) were used to compare the mRNA levels in transgenic mouse lines with those of wild-type controls of the same age. The oligomers were labeled at the 3'-end using terminal deoxynucleotide transferase and $^{35}$S-dATP (NEN) and the procedure for hybridization histochemistry was essentially as previously described (Luque J M, Malherbe P, Richards J G. Localization of NMDA receptor subunit mRNAs in the rat locus coeruleus. Brain Res Mol Brain Res. 1995.2:224–32). Briefly, tissue sections were brought to room temperature for 1 h before carrying out the hybridization. The incubation buffer (50 μl) included: 4×SSC (standard saline citrate), 20% dextran sulphate, 0.25 μg/μl tRNA, 0.25 μg/μl PolyA, 0.25 μg/μl Herring sperm DNA, 50% deionized formamide, 0.1M dithiothreitol, 0.5× Denhard's solution and $^{35}$S-labelled probe (3×10$^5$ d.p.m.). Sections, covered with strips of Fujifilm®, were incubated in a humid chamber at 43° C. overnight. After removal of the strips, the sections were washed in solutions containing 1×SSC and 0.5×SSC for 15 min and twice for 15 min, respectively, at 58° C. An additional washing was performed in 0.5×SSC for 15 min at room temperature. After a dip in double-distilled water, sections were dehydrated in ethanol. The hybridization signal was quantified by first exposing the labeled sections to BAS-IP SR 2025 universal imaging plates which were then scanned in a Fujifilm BAS5000 high resolution phosphor imager and finally measured a MCID M2 image analysis system (imaging Research, St. Catherines, Ontario, Canada). The hybridization signal was expressed as photostimulated luminescence (PSL) per mm$^2$ (FIGS. 2 and 3).

2. In Vitro Binding Studies with 125I-β-Amyloid

The tissues from wild-type and transgenic mice were prepared as for hybridization histochemistry except that they were not fixed. The sections were incubated in vitro with 0.1 nM $^{125}$I-β-amyloid peptide (Amersham) for 2 h at 20° C., washed dried and exposed to tritium-sensitive imaging plates (BAS-TR2025) or x-ray film for 4–14 days.

3. Immunoblot Analysis

Figure 4:
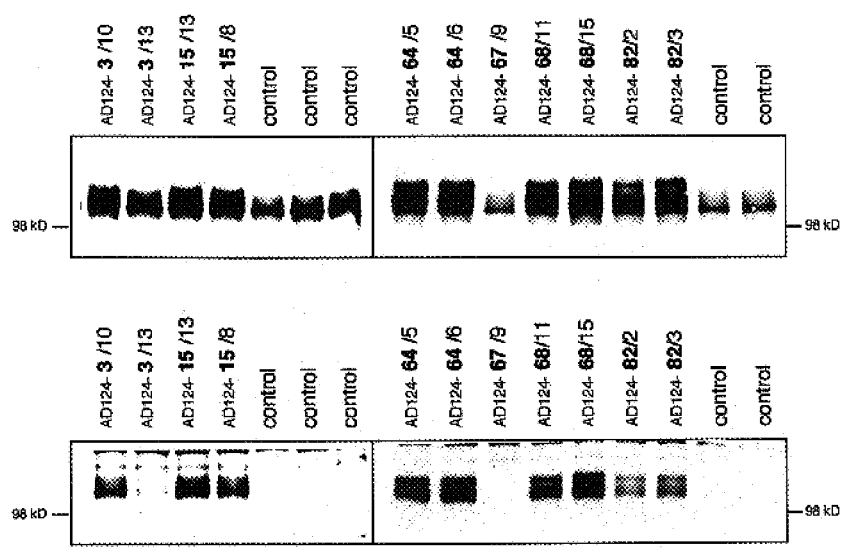
FIG. 4. Immunoblot. Total brain proteins from 2-months old heterozygous mice were immunoblotted with an antibody not differentiating between βAPP isoforms (22C11) and another antibody specific for kunitz-inhibitor-containing βAPP isoforms (anti-KPI).

Mice were killed by decapitation, brains removed, frozen in dry ice and kept at −70° C. until use. For the brain regions analysis, tissues from 3 littermates were pooled. Tissues were homogenized as already described (Malherbe et al. 1996). Extracted proteins (50 μg/slot) were separated on 10% Tris-Tricine gels, transferred to nitrocellulose and probed with either 22C11mAb, 1:200 (Boehringer-Mannheim) or rabbit anti-KPI at 0.8 μg/ml (Loffler J, Huber G. Beta-amyloid precursor protein isoforms in various rat brain regions and during brain development. J Neurochem. 1992 October;59(4):1316–24)(FIG. 4).

D. Summary of AD124 Transgenic Mice

In transgenic mouse lines AD 124 (βAPP mini-gene), a large imbalanced gene splicing resulting in substantially a higher level of βAPP$_{KPI}$ as compared to βAPP$_{695}$ was observed. The $^{35}$S-hybridization signal, using a probe specific for the OX-2 domain, for lines AD124/82, AD124/68, and AD124/64 were compared with AD124/15 and with 4 wild-type controls. The results of this analysis indicates that, for lines 82, 68, and 64, there was on average a 5–9-fold, 8–13-fold and 14–23-fold increase in transgenic whole brain, cortex and hippocampus CA-1, respectively. These values are in sharp contrast with those obtained with line 15, namely 2.5-fold, 3.5-fold and 4-fold increases respectively for whole brain, cortex and hippocampus CA-1. The heterozygous mouse lines AD124/64 and AD124/68 that expressed isoforms of hAPP-FAD(V717F) at high levels (detected by in situ hybridization and immunoblot analysis) were intercrossed to generate homozygous transgenic lines.

Example 2

BACE Transgenic Mice

Transgenic mouse lines express human BACE protein under the control of the mouse prion promoter. These mouse lines were denominated Prp-Asp.

A. Generation of the Human BACE Vector Contruct

The BACE 1 cDNA (SEQ ID NO:8) encoding protein sequence of SEQ ID NO:9 and comprising the complete open reading frame (ORF) plus flanking restriction sites was inserted into a mouse prion minigene vector where the prion ORF had been replaced by a suitable unique cloning site. The original minigene construct pPrPHg was described by Fischer et al. (Fischer M, Rulicke T, Raeber A, Sailer A, Moser M, Oesch B, Brandner S, Aguzzi A, Weissmann C. Prion protein (PrP) with amino-proximal deletions restoring susceptibility of PrP knockout mice to scrapie. EMBO J. 1996. 15:1255–64). In brief, the mouse prion ORF between an upstream KpnI site and a downstream NarI site was removed and replaced by a SceI restriction site. The BACE1 containing fragment was inserted by blunt ligation and its direction relative to the prion promoter verified by sequencing.

B. Generation of BACE Transgenic Mice

Figure 5:
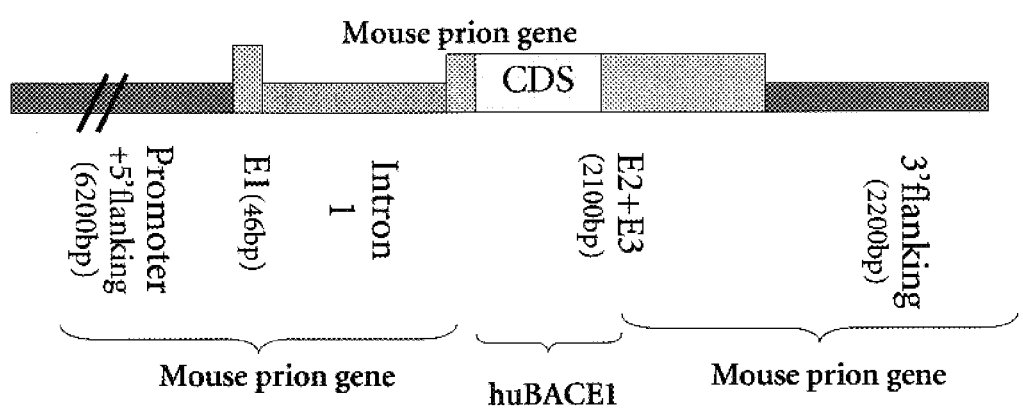
FIG. 5: Schematic diagram showing the Prp-Asp construct. E: exon.

The resulting fusion gene (FIG. 5) was freed of vector sequences, purified and microinjected using standard protocols into one-cell embryos of the cross C57B1/6×DBA/2 F2 mice. Ten transgenic founders (F0) were identified as having the transgenic by PCR analysis of tail DNA and subsequently crossed with wild-type C57B1/6 mice to establish transgenic lines. Briefly, genomic DNA was extracted following the protocol described by Laird P W, Zijderveld A, Linders K, Rudnicki M. A, Jaenisch R, and Berns A. Simplified mammalian DNA isolation procedure. Nucleic Acids Res. 1991. 19, 4293. PCR was run at 30 cycles: 95° C.×30 seconds, 59° C.×1 minute, 72° C.×1 minute; followed by 72° C.×5 minutes, using prion sense (Seq ID NO:10) and BACE anti-sense (Seq ID NO:11) primers. Eight out of the ten founders had integrated the transgene in the germ line and eight transgenic lines could be established.

Positive mice from the F1 generation were sacrificed in order to characterize the transgenic lines at the DNA level (Southern blot), RNA level (Northern blot and RT-PCR) and protein level (Western blot).

C. Characterization of BACE Transgenic Mice

1. Southern Blot Analysis

Transgene copy number was determined by Southern blotting using as references known amounts of transgene fragment mixed to genomic DNA isolated from nontransgenic littermates. Ten μg of genomic XbaI restriction fragments were fractionated by gel electrophoresis and blotted onto Nylon membranes (Roche Molecular Biosciences). A 1.1 kb DNA probe (XmnI digestion fragment of the transgene) was labeled with [$^{33}$P]dCTP by the random primer method using the Ready-to-Go DNA labeling kit (Pharmacia Biotech). Hybridization was performed overnight at 65° C. in 6×standard saline citrate, 10% dextran sulfate, 0.5% SDS. Blots were washed in 2×standard saline citrate (+0.1% SDS) at 65° C. for 20 minutes followed by a second wash at 65° C. in 0.2×standard saline citrate (+0.1% SDS). Blots were imaged with a Phosphorimager and quantified using the ImageQuant software.

2. mRNA Quantification by RT-PCR (Taqman)

Total RNA was isolated from brains using a commercial FastaRNA BIO101 kit, following the recommendations of the manufacturer. To ascertain RNA integrity, 10 μl of the resuspendend RNA pellet was mixed with RNA loading buffer and separated by electrophoresis on a denaturing 1.2% formamide/agarose gel. Ethidium-bromide-stained RNA fragments were visualized by UV transillumination. The extracted RNA was stored at −80° C. until use.

RNA was reverse transcribed using the Superscript™ Preamplification System (Life Technology). From each mouse brain, 20 μg of total RNA was mixed with 2 μl of oligo (dT)$_{18-20}$ primers (100 pmol/μl) and ddH$_2$O DEPC in a total volume of 22 μl and heated at 70° C. for 10 min. The mixture was then chilled on ice and incubated with 8 μl 5×reverse transcriptase buffer (250 mM Tris-HCl, pH 8.4, 375 mM KCl, 15 mM MgCl$_2$), 2 μl dNTP mix (10 mM), 4 μl 0.1 M dithiothreitol, and 4 μl of Superscript II RT Moloney Murine Leukemia virus reverse transcriptase (200 U/μl) at 42° C. for 60 min. The reaction mixtures were further incubated for 5 min at 95° C. and diluted to a final volume of 100 μl with ice-cold ddH$_2$O. The cDNA was stored at −20° C. until use.

Real-time PCR with SyBr Green detection was used to quantitate human BACE mRNA because it does not require oligonucleotide probes. Furthermore, upon binding to double-stranded DNA during strand elongation, SyBr Green fluorescence is greatly enhanced, making this method more sensitive than other approaches. First, the prepared cDNA (2 μl) was subjected to a differential polymerase chain reaction in the presence of the 5' and 3' human BACE primer pair. Mouse GAPDH was used as endogenous control (Leutenegger C M, Mislin C N, Sigrist B, Ehrengruber M U, Hofmann-Lehmann R and Lutz H. Quantitative real-time PCR for the measurement of feline cytokine mRNA. Vet Immunol Immunopathol 1999; 71: 291–305) to standardize the amount of cDNA added to the reaction. The following specific primer pairs were designed using Primer express software: for human BACE: sense primer (SEQ ID NO:12) and antisense primer (SEQ ID NO:13), and for muGAPDH: sense primer (SEQ ID NO:14) and antisense primer (SEQ ID NO:15). For quantitative PCR reactions, the following components were used: 2.5 μl×10 SyBr Green buffer, 3 μl MgCl$_2$ (25 mM), 2 μl dNTP mix containing dUTP (12.5 mM), 0.125 μl Amplitaq Gold DNA polymerase (5 U/μl), 0.125 μl Amp Erase UNG (1 U/μl) to avoid carry over of amplified DNA, 0.1 μl sense primer (50 nM), 0.1 μl antisense primer (50 nM), 15.25 μl ddH$_2$O, and 2 μl (20 ng) of template cDNA, in a total reaction volume of 25 μl. Quantitative PCR was performed in an optical 96-well plate (PE Applied Biosystems, CA) using a Perkin Elmer 7700 sequence detector. The PCR reaction consisted of the following steps: 1) 50° C. for 2 min to prevent carry over of DNA; 2) 95° C. for 10 min to activate ampliTaq Gold polymerase; 3) 50 cycles each consisting of 95° C. for 15 sec, 60° for 15 sec, and 72° C. for 45 sec. In addition to the quantitative detection of the amplified DNA fragments by fluorescence, DNA was mixed with loading buffer and separated on 3% agarose gels by electrophoresis. Ethidium bromide-stained DNA fragments.

3. mRNA Quantification by Northern Blot mRNA purified from 50 μg of total RNA (mRNA isolation kit; Roche Molecular Biochemicals) was separated on a 0.7% formaldehyde-agarose gel. RNA was then blotted onto a Hybond$^+$ membrane (Amersham Pharmacia Biotech) and hybridized to a mixture of 60 bp single-stranded oligonucleotide probes specific for RNA of the human BACE transgene beginning at nucleotide 30 (probe 659, SEQ ID NO:16), at nucleotide 570 (probe 660, SEQ ID NO:17), at nucleotide 1186 (probe 661, SEQ ID NO:18) of human BACE open reading frame. Probes have been 3'end-labeled by the terminal deoxynucleotidyl transferase reaction with alpha-[$^{32}$P] dATP (6000 Ci/mmol; Amersham Pharmacia Biotech) dATP for 60 min at 37° C., following standard procedure.

Hybridization was done in Rapid Hybridization Buffer (Amersham Pharmacia Biotech) for 2.5 hours at 65° C. Blots were washed in 2×SSPE (0.1% SDS) at room temperature for 10 minutes, followed by a second wash for 15 minutes at 65° C. and 2 more washes for 10 minutes in 1×SSPE (0.1% SDS) at 65° C. Membranes were exposed overnight on Phosphoimager for quantification. Hybridized probes were stripped from the blots by boiling in H20/0.1% SDS. Following the same protocol, the blots were then hybridized for 90 minutes at 60° C. with a [$^{32}$P] labeled single-stranded oligonucleotide probe specific for RNA of the mouse β-actin (SEQ ID NO:19). After the washing steps, membranes were exposed overnight on Phosphoimager.

4. Protein Quantification by Western Blot

Mice were killed by decapitation, brains removed and halved in a sagittal plane before freezing in dry ice. Fozen brains were kept at −70° C. until use. Half brains were homogenized in 1 ml 50 mM Hepes buffer pH 7.3 containing 0.1% Triton X-100 and 1% inhibitorcocktail III (Pierce). The proteins contained in 5 μl of each sample were fractionated by sodium dodecyl sulphate-polyacrylamide gel electrophoresis using 4–20% Novex (Invitrogen) gels. Proteins were transferred onto Hybond ECL membranes (Amersham), membranes were blocked by overnight incubation in PBS 0.05% Tween 20 (V/V) containing 20% New born Bovine Serum (NBS) and incubated for 1 h at room temperature with mAb BSC-1 specific for BACE (Grüninger-Leitch F, Schlatter D, Küng E, Nelböck P, Döbeli H. Substrate and Inhibitor Profile of BACE (beta-Secretase) and Comparison with Other Mammalian Aspartic Proteases. J. Biol. Chem. 2002 277: 4687–4693) diluted 1/1000 in PBS 0.05% Tween 20, 5% NBS. Binding of the primary antibody was detected with horseradish peroxidase conjugated anti-IgG antibody (Amersham) followed by enhanced chemiluminescence detection system (Amersham) according to the manufacturer's instructions.

For each transgenic line, the level of BACE was analyzed in two mice and compared to the level of endogenous BACE as measured in non-transgenic littermates. Line 13 and 24, the two highest expressing lines were estimated to express human BACE at levels corresponding to 5–10 fold the amount of endogenous mouse BACE. Line 10 which was defined as a low expressing transgenic line expressed human BACE at levels of about 2 fold the endogenous BACE levels (FIGS. 6A and 6B).

D. Summary of Prp-Asp2 Transgenic Mice

Mouse lines expressing human beta-secretase were analyzed at the DNA level for the determination of transgene copy number (Southern blot); at the RNA level for the quantification of transgene mRNA (Northern blot, RT-PCR), and for the quantification of BACE transgenic protein (Western blot; FIG. 6B). As shown in FIG. 6A, there was a good coorelation between the transgene copy number at the DNA level, the level of BACE mRNA transcripts and the levels of BACE proteins: Transgenic lines having integrated only one copy of the transgene, have BACE transcripts ranging from 10–30% of the levels of actin transcripts and BACE protein levels equivalent or only slightly enhanced when compared to non-transgenic mice; the high expressing transgenic lines have integrated from 5 to 20 copies of the transgene and have BACE transcripts at levels equivalent or double the actin transcript levels. Following this analysis, lines 13 and 24 were selected as high BACE expressor lines and line 10 as low BACE expressor line for backcrossing in the C57B1/6 background.

Example 3

BACE and APP London Double Transgenic Mice

A. Crossbreeding of AD124 Transgenic Mice Overexpressing Human APPV717F with Prp-Asp Transgenic Mice Overexpressing Human BACE Following standard crossbreeding protocols (male/female ratio of 1:1 or 1:2), APPV717F high expressor transgenic line AD124/68 was crossed with BACE high expressor transgenic lines Prp-Asp13 or Prp-Asp24. The first type of crossbreeding involved homozygotic APPV717F mice and heterozygotic Prp-Asp transgenic mice leading to bigenic littermates (APPV717+/− and BACE+/−) and singly transgenic littermates (APPV717+/−). The second type of crossbreeding involved heterozygotic APPV717F transgenic mice and heterozygotic Prp-Asp transgenic mice resulting in the generation of non-transgenic littermates (APPV717−/− and BACE−/−), bigenic littermates (APPV717+/− and BACE+/−), singly transgenic littermates (APPV717+/−), and singly transgenic littermates (BACE+/−). Mouse genotype was confirmed using PCR with tail DNA.

B. Characterization of Double Transgenic Mice

1. Organotypic Slice Cultures of Cerebellum

The preparation of brain slices was performed following a protocol by Metzger et al. (Metzger F, Kapffiammer J P. Protein kinase C activity modulates dendritic differentiation of rat Purkinje cells in cerebellar slice cultures. Eur J Neurosci. 2000 12:1993–2005). Shortly, post natal day 8–10 mice were decapitated and the brain was aseptically removed. The cerebellum was dissected in ice cold medium (MEM with 2 mM glutamax I, Life Technologies) and the meninges were carefully removed. Sagittal slices of 0.4 mm were cut using a McIllwain tissue cutter (Bachofer, Germany), separated with fine forceps, and transfered onto humidified transparent membranes (Millicell-CM, Millipore). Three slices were cultured on one filter (30 mm diameter) on top of 0.7 ml Neurobasal A medium with 2% (v:v) B27 additive (all Life Technologies). The slices were cultured for 8 days at 37° C. in a 5% $CO_2$ atmosphere. The culture medium was exchanged on day (DIV) 1, 3, 6, and 8 and analysed for sAPP alpha, sAPP beta and A-beta 40.

Figure 7A:
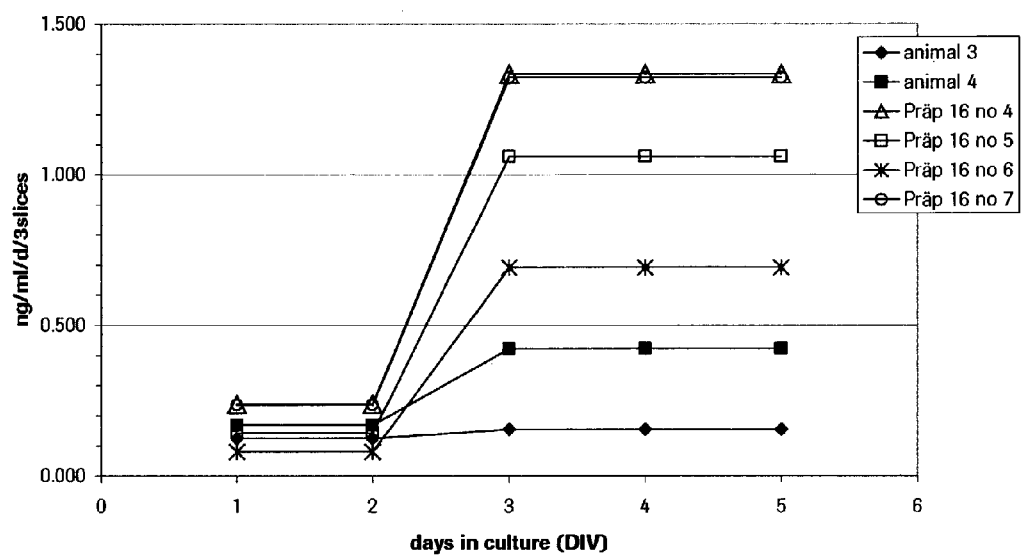
FIG. 7: Levels of amyloid fragments in supernatants of organotypic slice cultures of cerebellum originating from 10 days old mice. Panel A: A-beta 40 production in spent culture medium of brain slices from [BACE×APP London] double transgenic mice, APP London single transgenic mice and wild type mice. Animal 3 and 4 are non-transgenic controls, Prap 16, No. 6 is from APP London single transgenic mouse and Nos. 4, 5, and 7 are from [BACE×APP London] double transgenic mice. Panel B: Levels of A-beta 40, sAPP alpha and sAPP beta measured in spent culture medium of brain slices from one litter containing [BACE× APP London] double transgenic mice [#52] and APP London single transgenic mice [#49, #50, #51, #53].
Figure 7B:
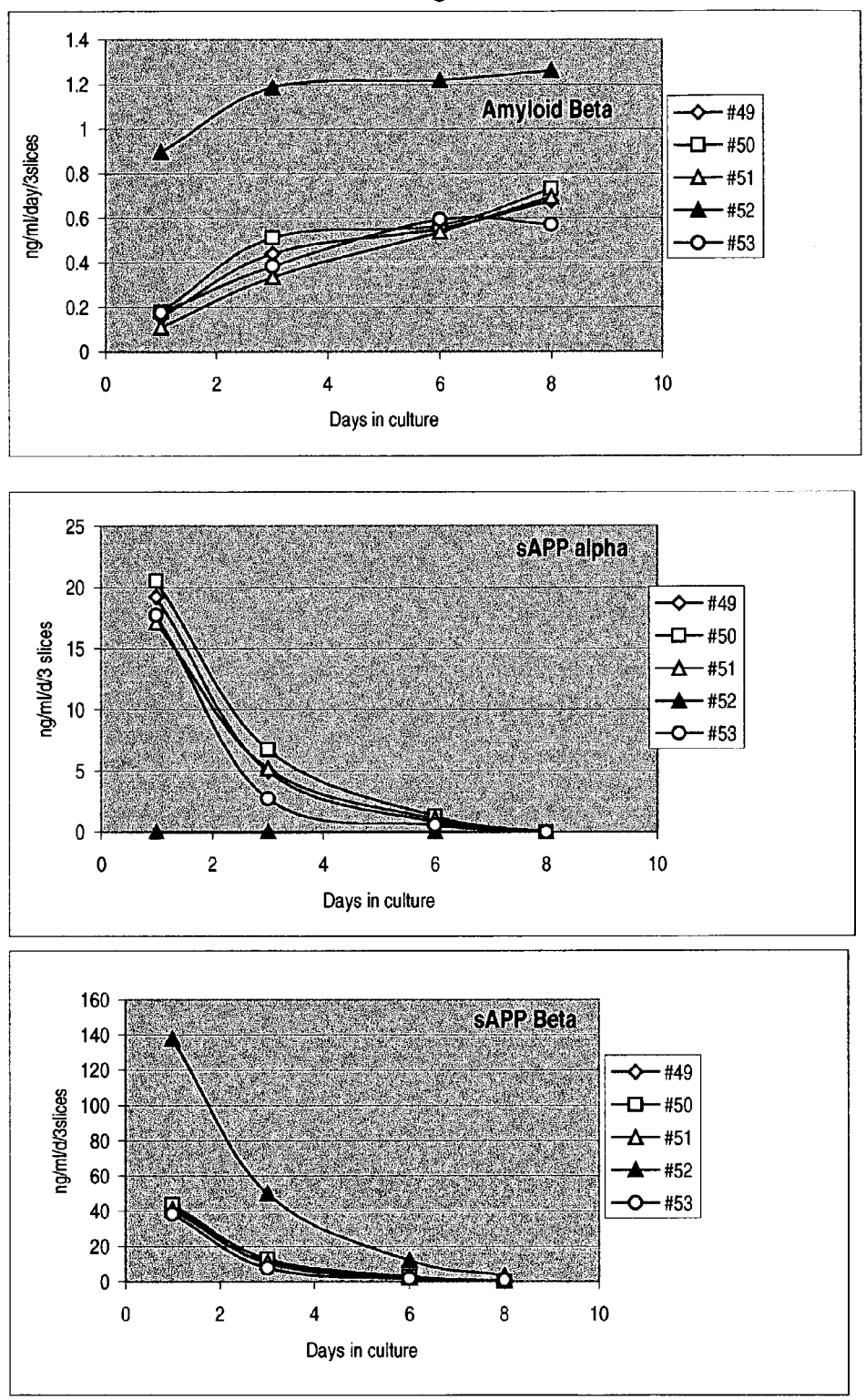

The production of A-beta 40 in culture supernatant of cerebellum slices from wild-type, APP London single transgenic and [APP London×BACE] double transgenic mice was monitored (FIG. 7A). An increase of A-beta 40 peptide is clearly seen after 3 days of culture for APP London single and [APP London×BACE] double transgenic mice. The APP London single transgenic mouse shows A-beta 40 levels of about 0.7 ng/ml/day whereas all double transgenic mice show levels above 1 ng/ml/day. Confirmation of those results and extension of the analysis to the assessement of sAPP alpha and sAPP beta fragments was performed with supernatants from brain slices originating from one litter (FIG. 7B) containing single APP London and double [APP London×BACE] transgenic mice (resulting from the cross between a homozygotic father APP London and a heterozygotic mother BACE). Double [APP London×BACE] transgenics show increased levels of sAPP beta when compared to APP London littermates. The level of sAPPalpha fragment was below detection limit in [APP London×BACE] double transgenic mice brain slices; in comparison, levels between 15 and 20 ng/ml/day were measured after 1 day of culture for APP London single transgenic mice. These results show that the over-expression of beta-secretase in APP London single transgenic mice induces a preferential cleavage of APPV717F at the beta cut as demonstrated by the lack of sAPPalpha fragment detection and the increase of sAPPbeta. The concomittent increase of the 12 kDa fragment which is the substrate for the gamma-secretase leads to increased levels of pathogenic A-beta peptide.

2. Extraction of Amyloid Fragments from Mouse Brains for Quantification in ELISA Mice were sacrificed and their brains removed. One cerebral hemisphere was homogenized using FastPrep homogenization Tubes (Qbiogene, Carlsbad, Calif.) in 1 ml of DEA buffer (2% diethanolamine, 50 mM NaCl). Supernatants containing soluble amyloid were collected after centrifugation and neutralized to pH 8 with 1M Tris-HCl as already described (Savage M J, Trusko S P, Howland D S, Pinsker L R, Mistretta S, Reaume A G, Greenberg B D, Siman R, Scott R W. Turnover of amyloid beta-protein in mouse brain and acute reduction of its level by phorbol ester. J Neurosci. 1998. 18: 1743–5). To extract insoluble amyloid, pellets were resuspended in 0.5 ml 9M urea, incubated overnight under rotation at 4° C. and supernatants collected after centrifugation. Both types of supernatants (collected after either DEA or urea extraction) were tested in ELISA.

3. Antibodies Used in ELISA for the Detection of Amyloid Fragments

6E10 and 4G8 monoclonal antibodies (mAbs) are commercially available (Senetek, Maryland Heights, Mo.). The BAP-1 antibody is specific for the epitope A-beta 4-7 which is present in soluble APP alpha, but not in soluble APP beta. Monoclonal antibodies BAP17 and BAP24 are specific for amyloid peptide A-beta 40, whereas monoclonal antibody BAP15 is specific for amyloid peptide A-beta 42 (Brockhaus M, Grunberg J, Rohrig S, Loetscher H, Wittenburg N, Baumeister R, Jacobsen H, Haass C. Caspase-mediated cleavage is not required for the activity of presenilins in amyloidogenesis and NOTCH signaling. Neuroreport. 1998. 9:1481–6). Monoclonal antibody ABS-1 was developed by immunizing with and screening against soluble recombinant human APP alpha. The detecting antibody rbVKM was developed by immunizing a rabbit (New Zealand strain) against the peptide CISEVKM coupled to keyhole limpet hemocyanin (Pierce, Rockford, Ill.) that was previously activated with N-hydroxy succinimidyl-maleinimido propionate (Pierce). The peptide conjugate was emulsified in Freunds complete adjuvants (Difco) and injected at 4 sites subcutanously. The injections were repeated 3 times at 4 weeks intervals using Freunds incomplete adjuvants (Difco). A high titered rabbit serum was obtained. It was purified by affinity chromatography on sulfolink gel (Pierce) to which the peptide CISEVKM had been coupled according to the instructions of the manufacturer. Since recombinant sAPP alpha was void of reactivity in the assay for sAPP beta, it was considered to be specific for the C-terminal neoepitope that is generated by the action of beta-secretase on APP.

When appropriate, the affinity purified antibodies were conjugated to horseradish peroxidase (Roche Molecular Biochemicals) using periodate activation (Nakane P K. Recent progress in the peroxidase-labeled antibody method. Ann N Y Acad Sci. 1975. 254:203–11). The antibody combination used for the detection of amyloid peptides in brain extracts are biotinylated 6E10 or biotinylated 4G8 monoclonal antibodies for the capture and HRP-BAP24 or HRP-BAP15 monoclonal antibodies for the detection of A-beta 40 and A-beta 42, respectively (Brockhaus et al. 1998). Soluble APP alpha- and APP beta-fragments were detected using biotinylated ABS monoclonal antibody for the capture and HRP-BAP1 monoclonal antibody or HRP-rbVKM for the detection, respectively.

4. ELISA

The ELISA was performed as previously described (Brockhaus et al. 1998). Briefly, microtiter plates (Nunc Maxisorb, Life Technologies) were coated first with streptavidin (Roche Molecular Biochemicals) at 5 µg/ml in 100 mM bicarbonate buffer then incubated with capture biotinylated mAb. After extensive washings of the plates with Tris buffered saline 0.05% Tween 20 (TBS-T), five fold serial dilutions of supernatants were added and incubated for 24 h at 4° C. in incubation buffer buffer (Tris 50 mM, NaCl 140 mM, EDTA 5 mM, NP40 0.05%, gelatin 0.25%, BSA 1%). The minimal dilutions were for culture supernatants: 1 fold, for DEA/Tris supernatants: 4 fold, for urea supernatants: 20 fold. The detection of the amyloid fragments was performed with Horse-Raddish Peroxidase (HRP) coupled monoclonal antibodies. Excess of HRP-mAbs was eliminated through three washing steps using TBS-T buffer. The tetramethylbenzidine (TMB) substrate was added to the plates for 5–10 minutes and the Optical Density was read at 450 nm after having stopped the reaction with sulfuric acid 2.5N. Purified A-beta or soluble APP fragments were used for calibration of the assay.

When homozygous APP London mice (line AD 124/68H) were tested in ELISA, a significant increase of mainly A-beta 42 peptide was detected from the age of 10 months with values of about 0.1 ng/mg brain, reaching levels of 2–12 ng/mg brain in 16 months old mice. The level of A-beta 40 peptide extractable from the homozygous APP London brain was much lower with values of 0.5 to 2.5 ng/mg brain.

Figure 8:
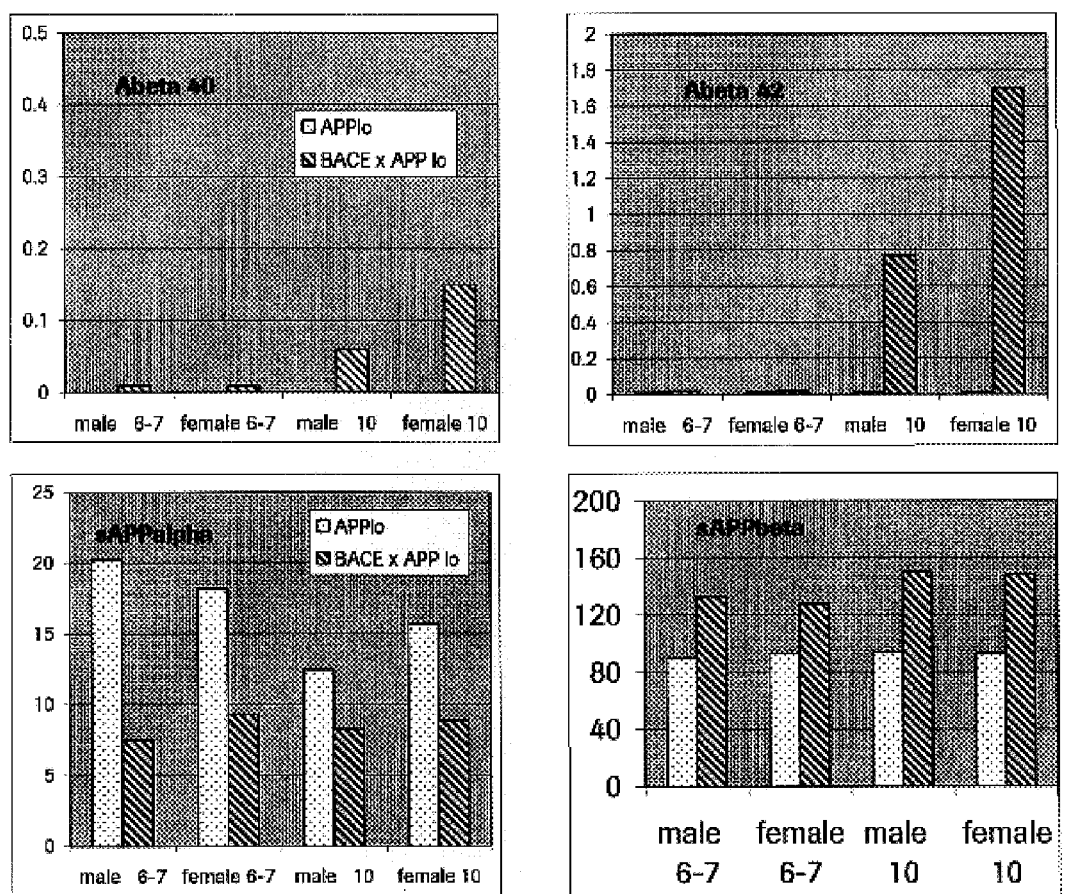
FIG. 8: Amyloid levels measured by ELISA in brain extracts from [BACE×APP London] double and APP London single transgenic mice at 6–7 and 10 months of age when no significant increase of A-beta peptides is found in single APP London control littermates which are heterozygotic for the transgene. At each time point, 3 males and 3 females were analyzed and the median value plotted.

The analysis of [BACE×APP London] double transgenic mice was performed at 6–7 and 10 months of age when no significant increase of A-beta peptides is found in single APP London control littermates which are heterozygotic for the transgene (FIG. 8). At each time point, 3 males and 3 females were analyzed and the median value plotted.

Significantly increased levels of A-beta 40 and A-beta 42 peptides (FIG. 8) were measured in [BACE×APP London] double transgenics. A-beta 42 peptide levels were about 10 fold higher than A-beta 40 peptide levels. Similar results were obtained with double transgenic lines for APP London×BACE line 13 or APP London×BACE line 24, ruling out an effect due to the transgene integration site. Thus, the increase of pathogenic amyloid peptide deposition is induced by the expression of beta-secretase. The levels of soluble APPalpha fragment and soluble APPbeta fragment in brains of [BACE×APP London] double transgenic mice were also measured (FIG. 8). When compared to single APP London control littermates, lower levels of sAPPalpha and higher levels of sAPPbeta fragments were measured in [BACE×APP London] mouse brains. Levels of soluble fragments did not show any significant time-dependent change irrespective of the transgenic line. In conclusion, the co-expression of beta-secretase in APP London overexpressing mice induced lower levels of sAPPalpha fragment, increased levels of sAPPbeta fragment and increased deposition of pathogenic amyloid peptides A-beta 40 and A-beta 42.

Figure 11:
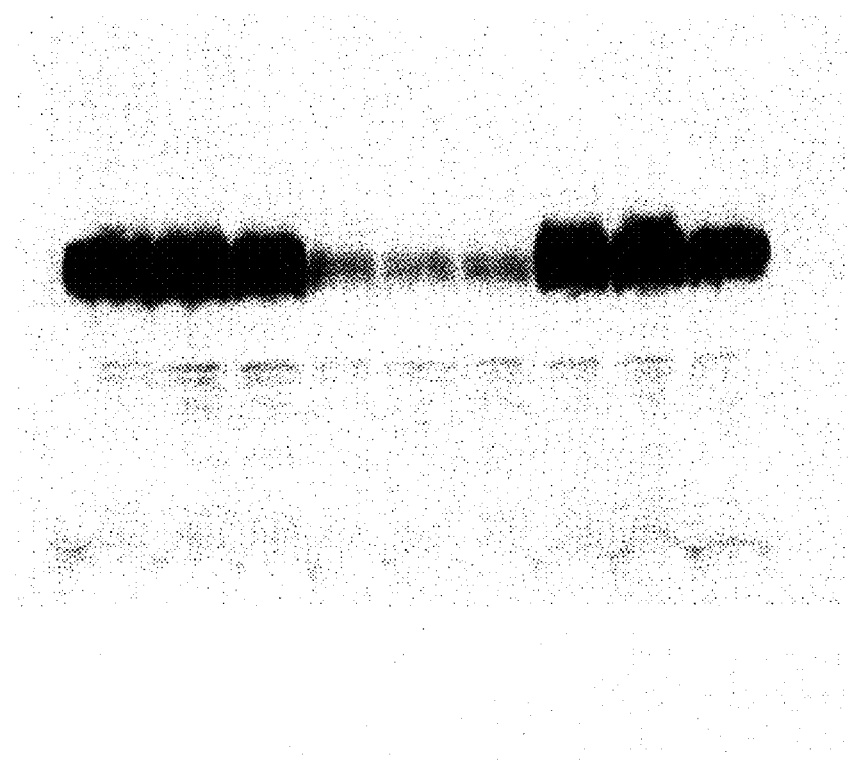
FIG. 11: BACE detection with BSC-1 mAb. Three mice (2 males and 1 female) were sacrificed at the age of 3 months from the [BACE line 13×APP London] double transgenic mice, from the APP London single transgenic mice (negative control for the human BACE) and from the BACE line 13 single transgenic mice. Samples 1, 2, and 3: [BACE×APP London] double transgenic mice; samples 4, 5, and 6: APP London transgenic mice; samples 7, 8, and 9: BACE transgenic mice.

5. Comparison of Beta-Secretase Levels in Single and Double Transgenic Mice by Western Blot Using the same methodology as described in Example 2, paragraph C4, beta-secretase levels were compared in double and single transgenic mice. For that purpose three mice (2 males and 1 female) were sacrificed at the age of 3 months from the [BACE line 13×APP London] double transgenic mice, from the APP London single transgenic mice (negative control for the human BACE) and from the BACE line 13 single transgenic mice. No significant difference was observed between the levels of beta-secretase detected in the [BACE line 13×APP London] double transgenic mice and the levels detected in the parental BACE 13 line (FIG. 11). These results show that transgenic overexpression of human BACE is not impaired by the overexpression of APP London.

6. Western Blot Analysis of Transgene Expression and Processing in Double Transgenic Mouse Brain Brain tissue from transgenic or non-transgenic littermate control mice was homogenized on ice in 0.32 M sucrose solution containing protease inhibitors (Complete™, Boehringer-Mannheim, Germany) using FastPrep homogenization Tubes (Qbiogene, Carlsbad, Calif.). The protein concentration in the supernatant was measured using the BCA protein Assay (Pierce, USA). For APP and A-beta detection 25 µg of protein extract was denatured at 95° C. for 10 min in Novex NuPage loading buffer (Invitrogen). The proteins were fractionated by sodium dodecyl sulphate-polyacrylamide gel electrophoresis using 10% Novex NuPage (Invitrogen) gels. After transferring the proteins to a nitro-cellulose filter (Amersham), the filter was heated in PBS for 5 min to increase sensitivity subsequently blocked with 5% (w/V) non-fat dry milk in PBST (PBS, 0.05% (V/V) Tween 20) and incubated overnight at 4° C. with the antibody WO-2 at a concentration of 0.1 µg/ml. Binding of the primary antibody was detected with horseradish peroxidase conjugated anti-IgG antibody (Amersham) followed by enhanced chemiluminescence detection system (Amersham) according to the manufacturer's instructions.

Figure 9:
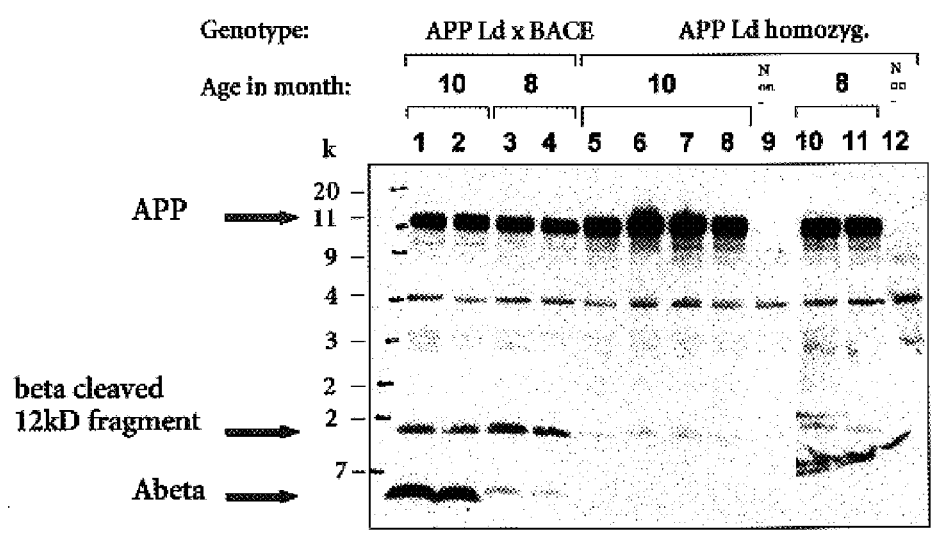
FIG. 9: Accumulation of A-beta in double transgenic mice. Analysis of APP, 12 kDa beta-cleaved fragment of APP and A-beta in brain homogenate of single and double transgenic mice at various ages using the human specific anti-A-beta antibody WO-2.

Brain homogenates of homozygous APP-London mice and double transgenic APP-London×BACE mice at 8 and 10 month of age were analyzed by Western-blot for APP and A-beta expression using the monoclonal antibody WO-2 (FIG. 9). This antibody readily detects APP and A-beta and does not crossreact with endogenous mouse APP since no signal is detectable in the lane corresponding to the non-transgenic mice (FIG. 9, lane 9 and 12). Same amounts of total protein were loaded in each lane. Intensity of the full-length APP band at 120 kD is higher in the homozygous APP London mice reflecting the additional copy of the transgene. In double transgenic mice expressing APP and beta-secretase, the 12 kD beta-secretase fragment of APP is strongly increased due to expression of transgenic beta-secretase.

Intensity of the full length APP band at 120 kD and the 12 kD fragment is constant in mice at different ages. However, there is a strong accumulation of A-beta in double transgenic mice starting at the age of eight months. This increase in A-beta correlates well with the onset of amyloid plaques in the brain of the transgenic mice suggesting that the increase of A-beta detected by Western-blot resembles A-beta accumulated in amyloid plaques. In single transgenic APP-London mice no accumulation of A-beta can be detected at the age of 10 months. Clearly the co-expression of BACE and mutated APP strongly accelerates the accumulation of A-beta.

7. Histochemistry and Immunocytochemistry

Fluothane$^R$-anesthetised mice were fixed by transcardiac perfusion of 4% formaldehyde in PBS at 22° C. after which the brains were removed, halved in a sagittal plane and immersed in the same fixative for 24 h. One brain half was then cryoprotected overnight in 30% sucrose before freezing in dry-ice and the other half dehydrated and embedded in paraffin wax. Cryostat or paraffin sections were cut at 10 µm.

Fibrillar Aβ deposits were detected with Accustain$^R$ amyloid stain, Congo red (Sigma Diagnostics HT60). The following antibodies were used to detect antigenic sites with a Vectastain$^R$ ABC kit Elite and peroxidase (ImmunoPure® Metal Enhanced DAB Substrate Pierce 34065): BAP-2 (monoclonal mouse IgG1 raised against Aβ1–40; recognizes amino acids 4–7, Dr. Brockhaus); CD45 (activated microglia; clone IBL-3/16, Serotec MCA 1388); GFAP (activated astroglia; clone G-A-5, BioMakor 6077); apoE (apolipoprotein E; Chemicon AB 947); AT-8 (PHF-τ clone AT-8 Endotell BR-03); BSC-1(BACE; Grüninger-Leitch F et al. J. Biol. Chem. 2002 277: 4687–4693). For controls, peptide blocks or relevant isotype for poly- and monoclonal antibodies were used, respectively. For the digital imaging and processing of stained sections a ProgRes 3012 high resolution scanner camera (Kontron, Zeiss) and Adobe Photoshop software were used, respectively.

Figure 10A:
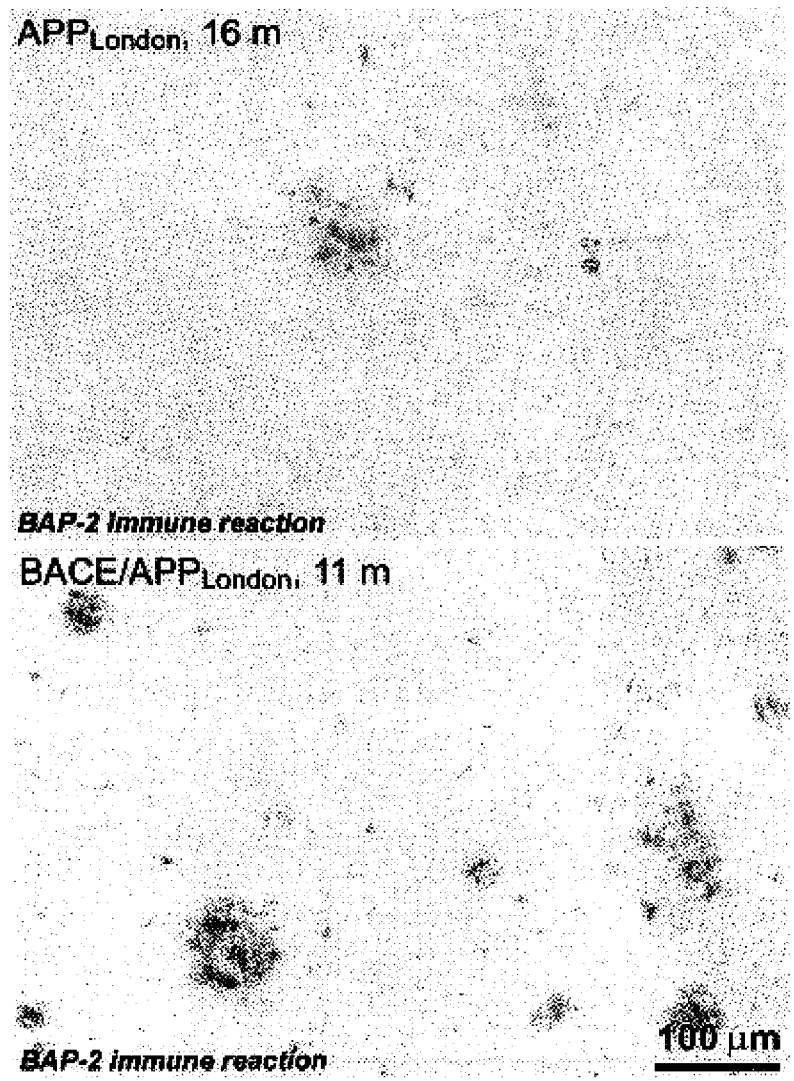
FIG. 10: Panel A. Amyloid plaques (as detected by BAP-2 monoclonal antibody (mAb) immunoreactivity) in the cortex of 11 months old [BACE×APP London] double transgenic mouse. A 16 months-old single transgenic mouse homozygotic for APP London is shown in comparison. Panel B. Detection of inflammatory markers: GFAP-immunoreactive astrocytes and CD45-immunoreactive activated astroglia; of amyloid plaques (BAP-2 mAb immunoreactivity); and of BACE (BSC-1 immunoreactivity) in the cortex of a 16 months-old [BACE×APP London] double transgenic mouse.
Figure 10B:
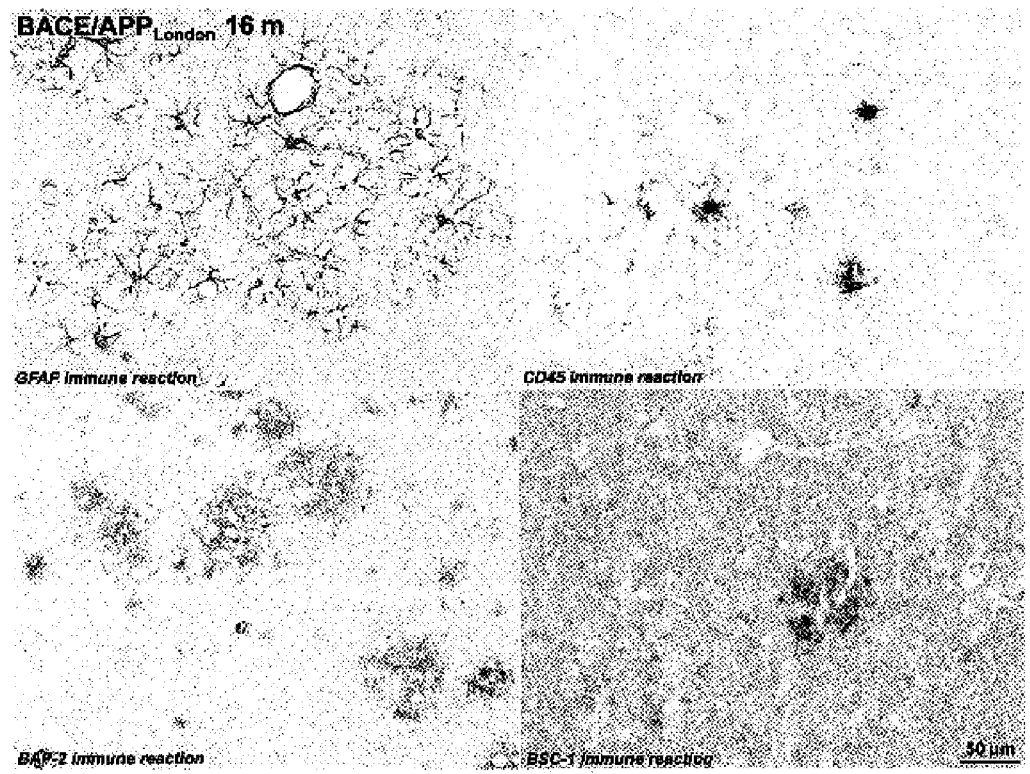

Amyloid deposition in plaque structures was clearly detected in 11 months old [BACE×APP London] double transgenic mouse (FIG. 10A). Some of the plaques were congophilic. Strong congophilic staining was also observed on vascular amyloid deposition. No significant difference in the brain distribution of amyloid deposits was observed between [BACE×APP London] double transgenic mice and APP LondonH single transgenics, but immunostaining using BAP-2 mAb showed a consistant stronger staining pattern on amyloid deposits from [BACE×APP London] double transgenic mice when compared to single transgenic mice suggesting some difference in the amyloid plaque structure or composition. Beta-secretase was detected most probably in association with the amyloid deposits as demonstrated by the positive immunostaining with BSC-1 mAb (FIG. 10B). Amyloid deposition detected in [BACE×APP London] double transgenic mice was also accompanied by the presence of inflammatory markers: GFAP and CD45 (FIG. 10B).

8. Immuno-Electron Microscopy

Cryofixation, Freeze-substitution and Low-temperature Embedding

Perfusion-fixed brain tissue, while immersed in fixative, was cut into approximately 100 µm thick sections using a vibratome and cryoprotected by immersion in increasing concentrations of glycerol (10–20–30% v/v) in 10 mM phosphate buffer, pH 7.4 for 0.5 h per concentration. Vibratome sections were carefully picked up by forceps and plunged into liquid ethane cooled by liquid nitrogen. Frozen tissue slices were stored in liquid nitrogen before being transferred to the pre-cooled chamber (–90° C.) of an automated freeze-substitution apparatus (AFS, Reichert, Austria). The tissue was immersed overnight in anhydrous methanol at –90° C., containing 0.5% (w/v) uranyl acetate. The temperature was allowed to rise to –45° C., at a rate of 6.7° C./h. Samples were washed three times with anhydrous methanol for 30 min each to remove residual water and excess uranyl acetate before infiltration with Lowicryl HM20 resin (Chemische Werke Lowi; Waldkraiburg, Germany). Infiltration with resin was done in mixtures of HM20 and methanol at vol. 1:1 and 2:1, each for 2 h, and pure HM20 for 2 h, 16 h and 2 h. Samples were processed in the flow through system of the Reichert AFS apparatus and polymerized by indirect UV irradiation (360 nm) for 24 h at –45° C., followed by UV-irradiation for 1 day at room temperature to achieve complete resin polymerization.

Immunolabeling of Resin Thin Sections

Ultrathin sections were prepared on a Reichert Ultracut S using a diamond knife (Diatome) and collected onto formvar/carbon-coated 200-mesh nickel grids. The sections were floated on 0.05 mol/L glycine in PBS for 15 min to inactivate free aldehyde groups and then on 2.5% (w/v) hen egg white albumin (Fluka) with 2.5% (w/v) bovine serum albumin (BSA, fraction V, Boehringer) in PBS for 15 min to block nonspecific binding sites. Sections were incubated with 10 µg/ml mAb BAP-2 in 2% BSA/PBS for 1 hour. After 6 washes in BSA/PBS, the sections were incubated with a secondary goat anti-mouse IgG (Amersham, Arlington Heights, Ill.), conjugated to 10 nm gold at 1:20 dilution in 2% BSA with 0.1% Tween 20 in PBS for 1 hour, and washed in BSA/PBS. For controls, sections treated with normal mouse serum were used, which resulted in a negligible background of not more than 10 gold particles in an area of 10 µm$^2$. The sections were postfixed in 2% glutaraldehyde in PBS for 5 min, washed, and stained with 4% aqueous uranyl acetate for 10 min, followed by lead citrate for 90 seconds. Electron micrographs were taken with a JEOL 1210 at 100 kV.

Ultrastructural Localization of Aβ

Figure 12A:
FIG. 12: Panel A: On-section immunogold labeling after cryofixation using an anti-A-beta monoclonal antibody (BAP-2) visualized by GAM secondary antibody conjugated to 10 nm colloidal gold. Labeling is found on fibrillar deposits within smooth muscle cells and fibril bundles penetrate into the basal membrane towards the endothelial cell layer (arrow). Panel B: On-section immunogold labeling after cryofixation using an anti-A-beta monoclonal antibody (BAP-2) visualized by GAM secondary antibody conjugated to 10 nm colloidal gold. Labeling is detected on extensive masses of accumulated A beta fibrils within the remnants of smooth muscle cells.
Figure 12B:
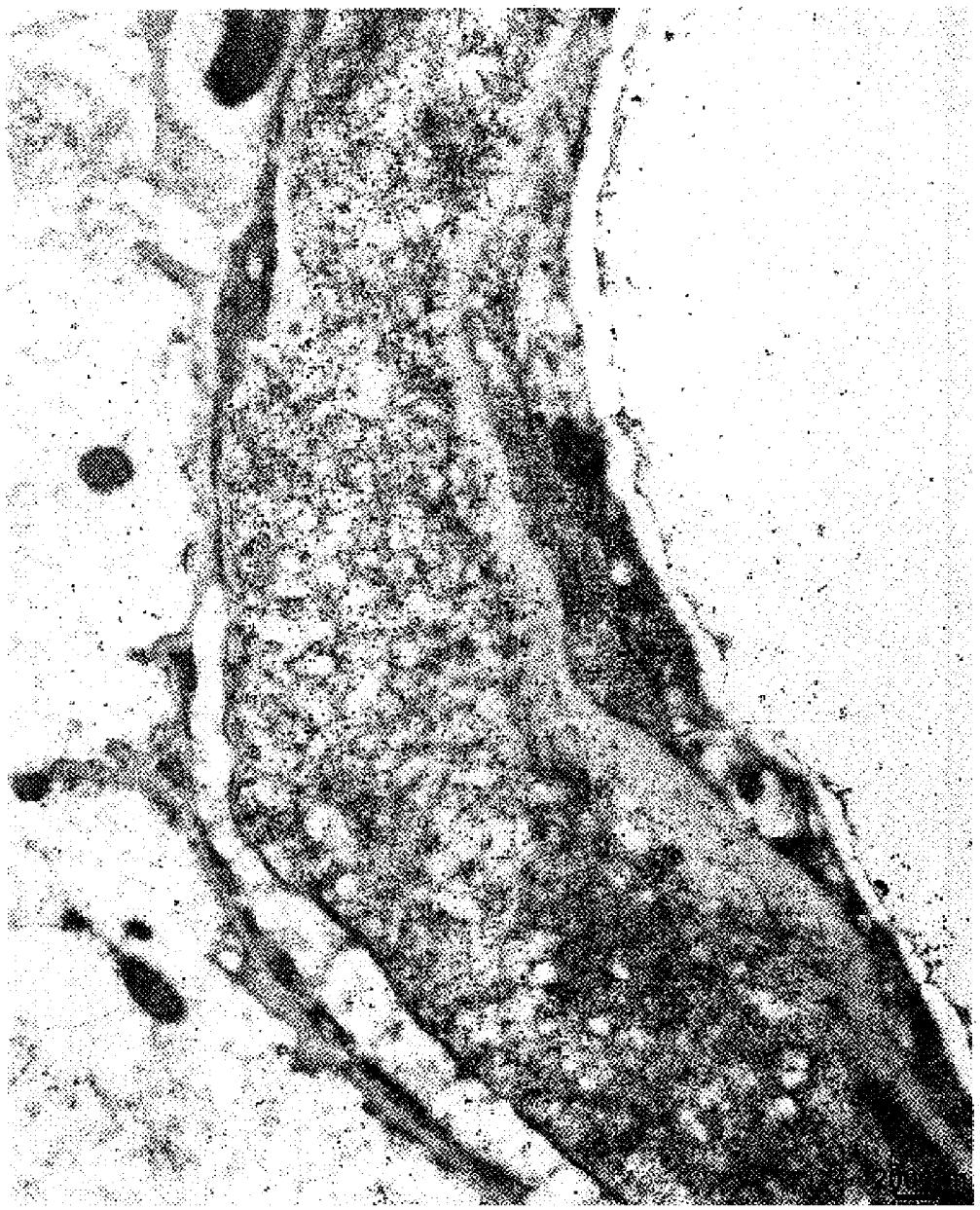

Immuno-electron microscopy was carried out on low temperature-embedded mouse brain tissue of 18 months old animals. The method combines the advantage of superior preservation of ultrastructure and antigenicity for efficient immunocytochemical staining. Immunogold labeling, using a monoclonal antibody against the N-terminal part of the A-beta-peptide (BAP-2), revealed fibrillar A-beta within the media of arteries and arterioles. Bundles of fibrillar A-beta occassionally penetrate into the basal membrane which might interfere with the integrity of the blood brain barrier (FIG. 12A). Fibrillar A-beta is found at considerable density at the layer of smooth muscle cells (FIG. 12B) that appears to increasingly accumulate fibrillar aggregates in analogy to cerebral amyloid angiopathy (CAA) in humans. In the used mouse model the frequency of CAA is considered to be slight to moderate depending on age. This process of increasing A-beta deposition may ultimately lead to ruptured blood vessels as observed in human CAA.

Figure 13:
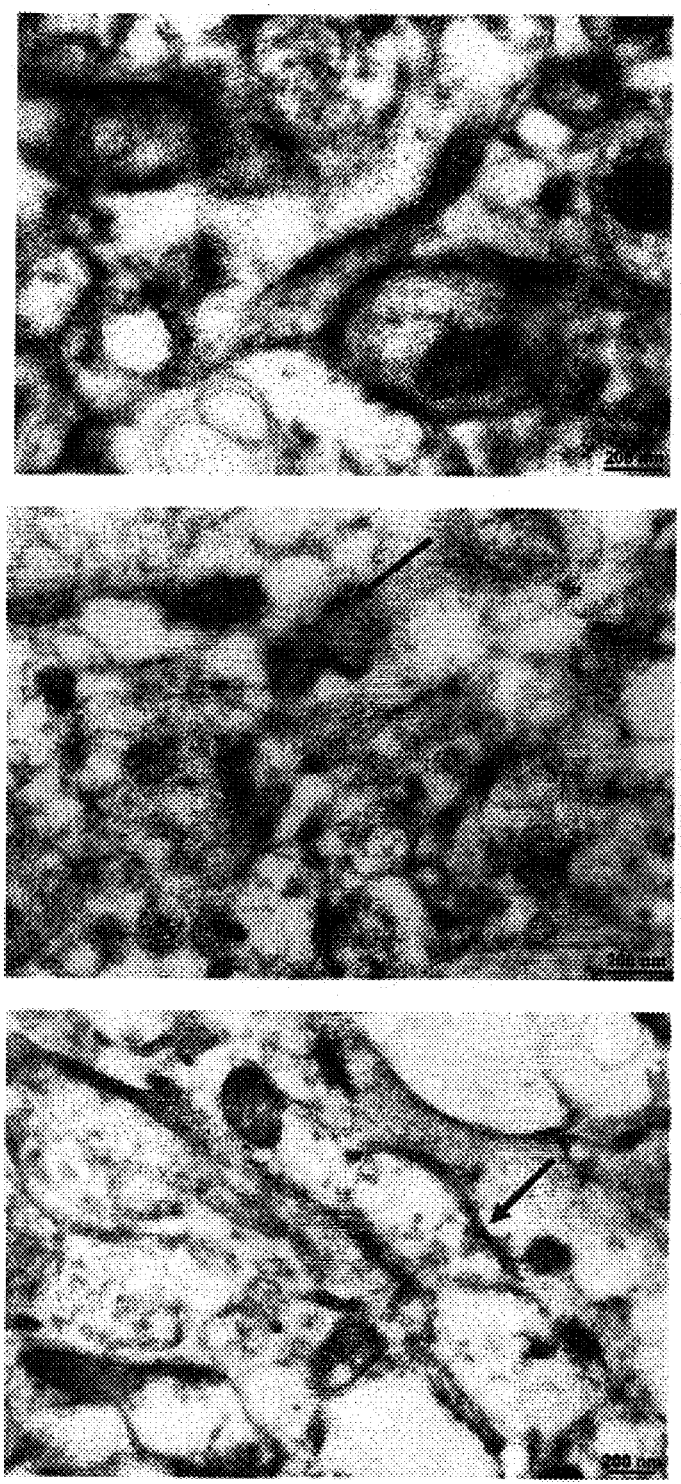
FIG. 13: On-section immunogold labeling after cryofixation using an anti-A-beta monoclonal antibody (BAP-2) visualized by GAM secondary antibody conjugated to 10 nm colloidal gold. The panel of electron micrographs show three different examples from areas within a diffuse amyloid plaque from the frontal cortex of an 18 months old BACE× APPlon transgenic mouse brain. Labeled A-beta is found on small patches near the plasma membrane of neurites and dentrites (arrow). Note that the labeled material has an amorphous ultrastructure that appears to be nonfibrillar.

Dense cored plaques, which can be detected by congo red staining are detectable at low frequency while diffuse A-beta deposits that are not stained by congo red but are detectable by immunohistochemistry are more frequent. The ultrastructure of A-beta within diffuse plaques was analysed by immuno-gold labeling against A-beta in the frontal cortex of 18 months old animals (FIG. 13). Immunoreactivity was found on discrete patches of electron-dense material adjacent to the cell membrane of neurites and dendrites. Remarkably, no clear fibrillar ultrastructure, as observed in the media of blood vessels is detected. This might indicate that this form of A-beta resembles early aggregation clusters that are intermediate precursors to the well-characterized mature A-beta fibrils. Indications for early A-beta aggregation that precedes significant neurodegeneration is particularly important to study the mechanism(s) of A-beta-mediated neurotoxicity and characterize therapeutics for the treatment of AD.

9. Behavioral Studies

Behavioural data for mice expressing APP London and [BACE×APP London] double transgenic mice (at 12 months) were compared with age-matched wild type mice. Mice were weighed weekly and general appearance was checked. All mice were individually housed. In addition, body temperature, coat appearance, secretory signs, body posture were also noted.

Neurological Tests

Wire manouvre: Mice were placed by forepaws on an elevated wire rod and the latency to fall was noted. Cut-off time was 60 s and the best score from 3 attempts was recorded.

Grip strength: Mice were forced to pull on a strain gauge and the release point is recorded. The best score from 5 attempts is recorded.

Rotarod: Mice were placed on a constant speed rotarod and the latency to fall was noted. Cut-off time was 120 s and the best score from 3 trials was taken. 2 speeds were used: 16 rev/min, 32 rev/min.

There was no difference in body weight between genotypes, although female mice had a lower body weight when compared with males this is typical (i.e. males are usually heavier than females). There was a small but significant reduction in grip strength in female hAPPLo and male hBACE/hAPPLo mice when compared with wild type controls. Horizontal wire performance was reduced in male mice expressing hAPPLo and in both male and female mice expressing hBACE/hAPPLo. Male hAPPLo mice spent significantly less time on the rotarod (32 rpm) compared with wild type controls. Overall there was no major impairment of motor performance (i.e. ataxia) detected in any of the genotypes (Table 1).

Locomotor activity: The mice were placed into a novel test chamber for a 1 h period which consists of a Plexiglas® box (20 cm×20 cm×27 cm) with sawdust bedding on the floor. The animals' movements were recorded using an electronic monitoring system (Omnitech Electronics Inc., Columbus, Ohio, USA). Movement of the animal results in interruption of an array of photobeams from vertically and horizontally located infrared sources placed around the test chamber. Total distance travelled (cm) and number of rears were measured.

Figure 14:
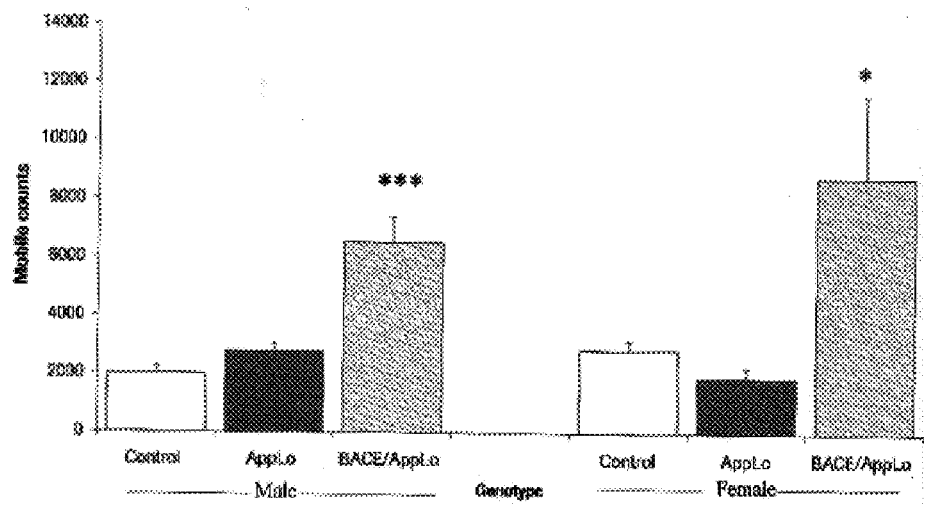
FIG. 14: Locomotor activity, as measured by mobile counts, of mice expressing hAPPLo and hBACE/hAPPLo and wild type controls. Data are expressed as mean±s.e.m. (two factor ANOVA (gender and genotype) followed where appropriate by a one factor ANOVA (genotype) for both males and females and a Newman Keuls post hoc:*$p<0.05$, ***$p<0.001$.

Both male and female mice expressing hBACE/hAPPLo had increased locomotor activity over the one hour test period, as demonstrated by a significant increase in total mobile counts during this period. Consistent with this, mobile time was also significantly elevated in male and female hBACE/hAppLo mice, and whilst not significant, a similar trend was seen in the total number of rear counts. Thus, both male and female mice expressing hBACE/hAPPLo were hyperactive when compared with wild type controls (FIG. 14).

Y-maze

Mice were placed in a Y-maze made of black perpex (each arm is 53 cm long, 15 cm wide and 30 cm in height) for 5 min. A camera was positioned above the maze and the animals were observed on a monitor in an adjoining room. The number of arm entries and their entry sequence was noted to calculate an alternation measure.

Figure 15:
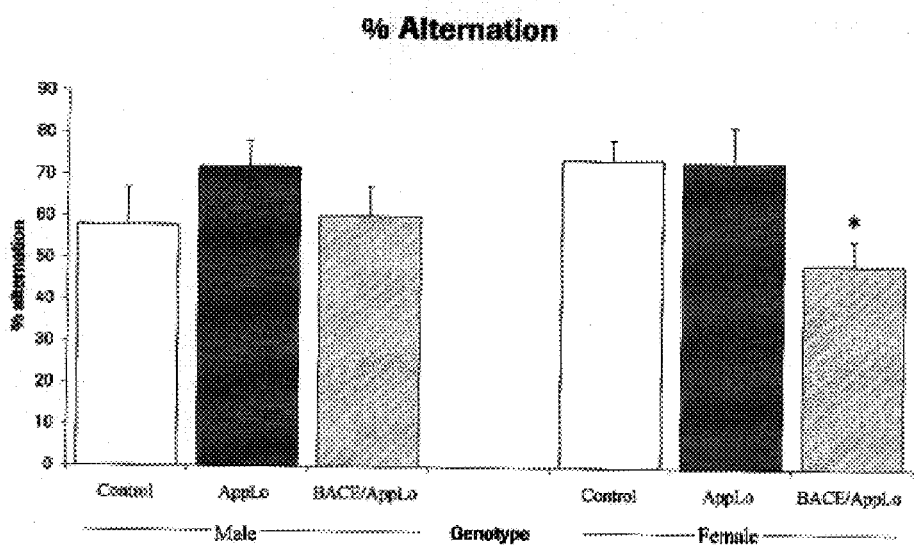
FIG. 15: Assessment of working memory, using spontaneous alternation in the Y maze, in wild type and mice expressing hAPPLo and hBACE/hAPPLo. Data are expressed as mean±s.e.m. (two factor ANOVA (gender and genotype) followed where appropriate.

There was no effect of genotype in male mice. However, female hBACE/hAPPLo mice showed a deficit in this task of working memory, as measured by a reduction in percentage alternation when compared with wild type controls (FIG. 15). Notably, there was no difference in percentage position bias between gender or genotype. Interestingly, whilst not significant, both male and female hBACE/hAPPLo mice showed a tendency for an increased number of arm entries, consistent with these mice being more active than wild type controls, as demonstrated previously in the locomotor activity test (see FIG. 14). Thus, female, but not male, mice expressing hBACE/hAPPLo were impaired in this task of working memory.

Morris Water Maze

The water maze consisted of a grey circular tank (1 m diameter) filled with water made opaque by the addition of a latex solution (E-308; Induchem, Voletswil, Switzerland). Pool temperature was maintained at 21+1° C. For the hidden platform task, the escape platform (8 cm diameter) was positioned 1 cm below water level in the centre of one of the pool quadrants. For the cued task, platform position was signalled by the addition of a small black flag which is positioned in the centre of the submerged platform. The walls surrounding the water maze were hung with posters and flags which serve as visual cues and are visible during all stages of training and testing. Movement of the mice within the pool was tracked and analysed with a computer based video tracking system (HVS Image, Hampton, UK).

For cued training, mice were placed in the pool facing the edge at one of four start positions (NE, SE, SW, NW), and were required to locate the flagged platform whose position varies across trials. Each mouse received a total of 12 trials (three trials per block, 2 blocks per day, 2 day duration). Intertrial intervals averaged 10 min, and maximum trial length was 60 s. If mice failed to find the platform within 60 s, they were guided to its position by the experimenter. All mice were allowed to remain on the platform for a 10 s period before being removed and returned to the homecage. The cued task was followed by the place task, in which mice were required to locate a submerged hidden platform whose position remained fixed throughout training. Platform location was balanced within groups. Each mouse received 8 blocks of training trials over four consecutive days (three trials per block, timing as per cued test) in which they were placed in the pool at one of four start positions, and allowed to locate the hidden platform. Assessment of spatial learning was conducted in probe trials performed both 30 min after block 4, and 24 h following the final trial. In each probe trial the platform was removed from the pool, and the path swam by each mouse recorded over a 60 s period.

In cued acquisition there was neither a gender and genotype nor gender, genotype and trials interaction indicating that visual acuity and motivation to find the escape platform was equivalent between genotypes.

Figure 16:
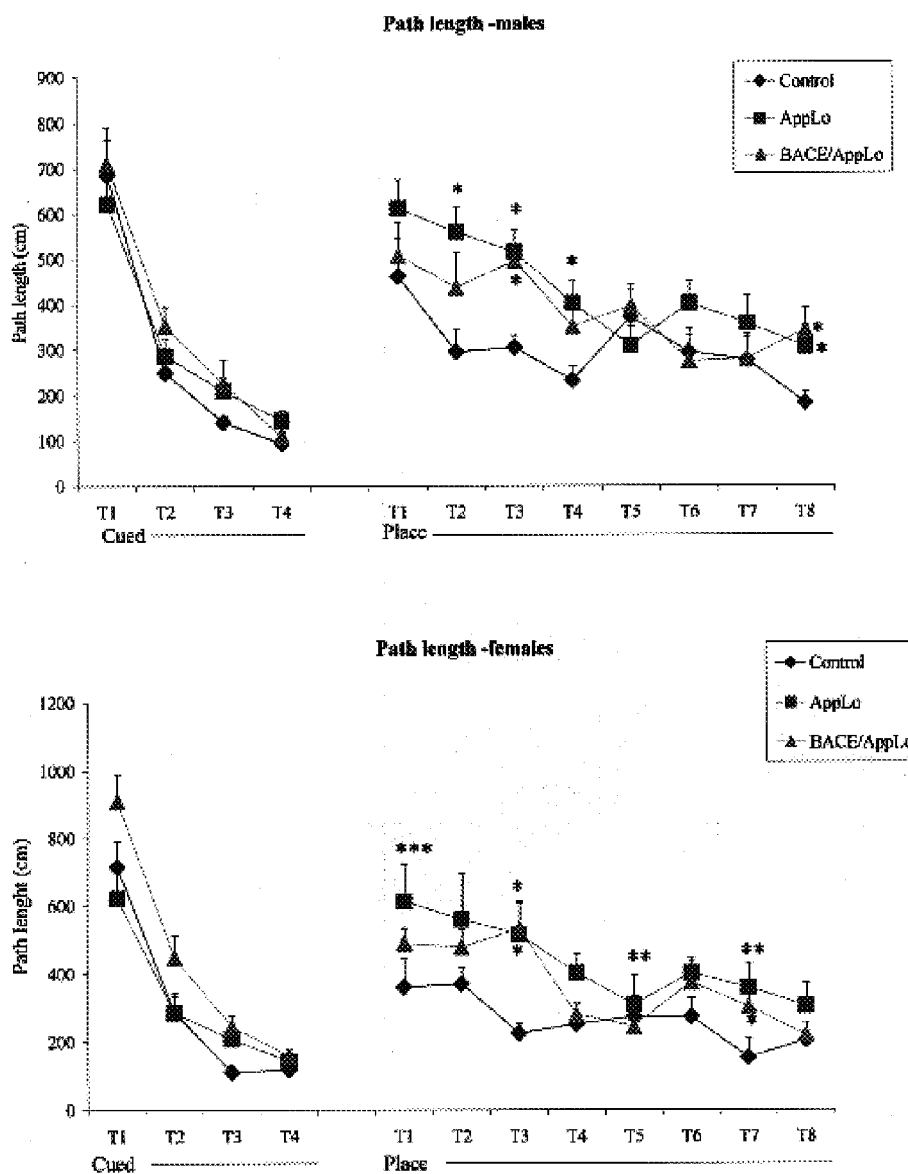
FIG. 16: Acquisition learning in the Morris water maze in wild type and mice expressing hAPPLo and hBACE/hAPPLo. Data are expressed as mean±s.e.m. (two factor ANOVA (gender and genotype) with repeated measured (trials) followed by a one factor ANOVA (genotype) for both males and females and a Newman Keuls post hoc:*$p<0.05$.

In place acquisition, in which mice were trained to locate a hidden platform, path length to the hidden platform was increased in male and female mice expressing both hAPPLo and hBACE/hAPPLo showing that these mice acquired the task more slowly than wild type controls (FIG. 16). Of note, latency to find the hidden platform was also significantly higher in both male and female hAPPLo mice, consistent with a reduced level of acquisition in these mice. However, male (but not female) hAPPLo mice demonstrated a reduced swim speed when compared with wild type controls, which could contribute to the increased escape latency.

Figure 17:
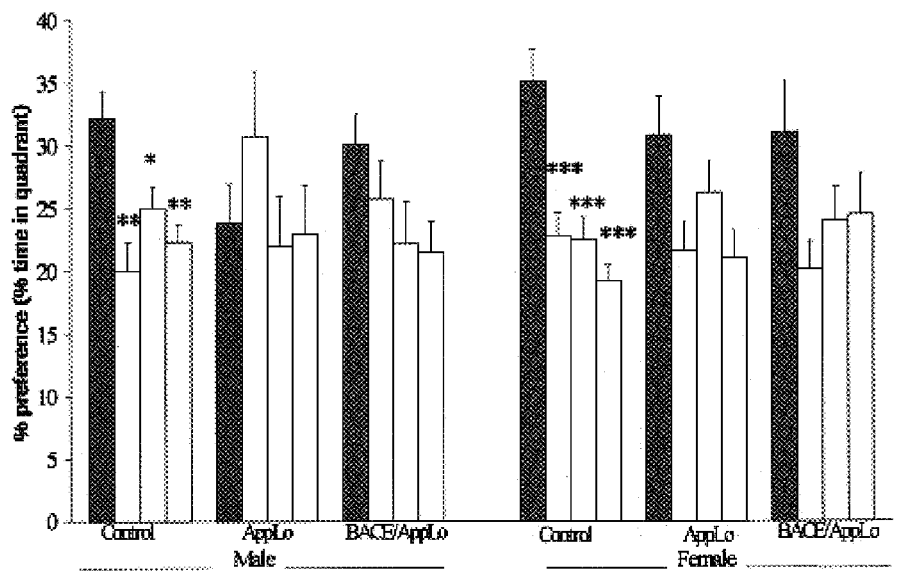
FIG. 17: Probe tests measuring the time spent in each quadrant during a 60 second period in which the hidden platform is removed from the pool, to assess how well the mice have learnt the platform position halfway through acquisition training (Panel A) and at the end of training (Panel B) as shown by the arrows in FIG. 3. Data are expressed as mean±s.e.m. (one factor ANOVA with repeated measured (quadrants) for each group followed where appropriate by a Newman Keuls post hoc:*$p<0.05$,$p<0.01$, *$p<0.001$.
Figure 17:
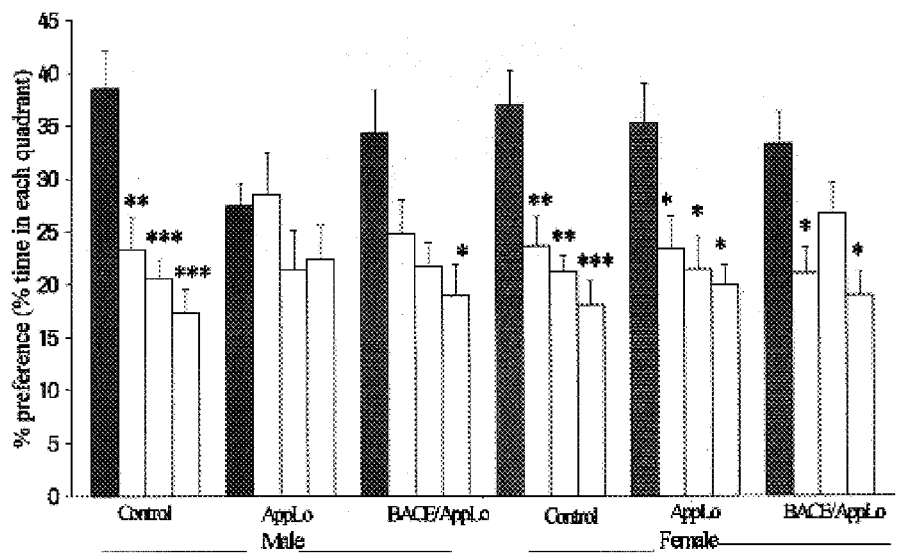

In the first probe test, performed halfway through training, both male and female wild type mice had learnt the position of the hidden platform such that they spent significantly longer exploring the quadrant in which the platform was located during training when compared with time spent in the other three quadrants (FIG. 17). Conversely, male and female mice expressing both hAPPLo and hBACE/hAPPLo spent equivalent times exploring all four quadrants showing they had not learnt the position of the hidden platform. In the second probe test, performed at the end of training, both male and female wild type mice spent significantly longer exploring the quadrant in which the platform was located during training showing that they had learnt the position of the hidden platform. Male mice expressing hAPPLo spend equal time exploring the four quadrants showing that they had not learnt the position of the hidden platform, in contrast, hAPPLo female mice had learnt the platform position. Both male and female mice expressing hBACE/hAPPLo showed a tendency towards spending more time in the quadrant containing the platform during training, although this was not significant in all cases, showing that these mice had not learnt the task to the same precision as the wild type controls.

Active Avoidance

Mice were placed into a 2-compartment chamber within which they could freely pass between compartments (San Diego Instruments, USA). Each trial began with the side currently occupied by the mouse being illuminated by a 10 s light (CS), which is used to signal a footshock (0.2 mA) of maximum duration 20 s. (NB. the mice never receive this shock duration for they either escape within 1s to the other (unshocked) compartment, or learn to avoid the shock altogether). This was followed by a variable timeout period (mean 20 s, range 15–25 s) (no light) in which the mouse can freely explore the chamber. Following the timeout, the next trial begins. Shock can be avoided either by a shuttle to the next compartment during the CS period, (i.e avoidance) or escape at any time during the shock presentation. Ten daily test sessions were run with each session consisting of 20 trials. The dependant measure is % avoidance.

Figure 18:
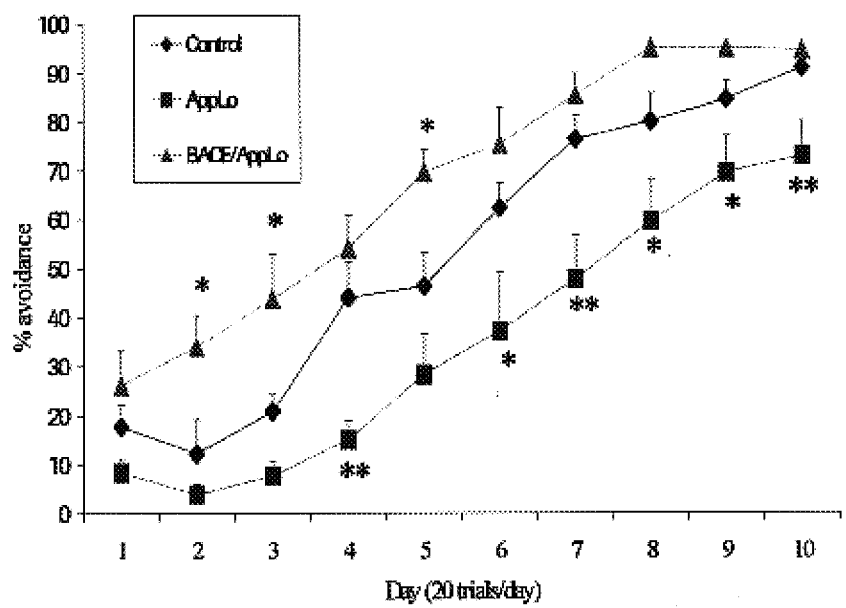
FIG. 18: Acquisition learning in the mice to actively avoid an unconditioned stimulus (US, 0.2 mA footshock) following the presentation of a conditioned stimulus (CS, light). Data are expressed as mean±s.e.m. (one factor ANOVA with repeated measured (platforms) for each group followed where appropriate by a Newman Keuls post hoc:*$p<0.05$, **$p<0.01$.
Figure 18:
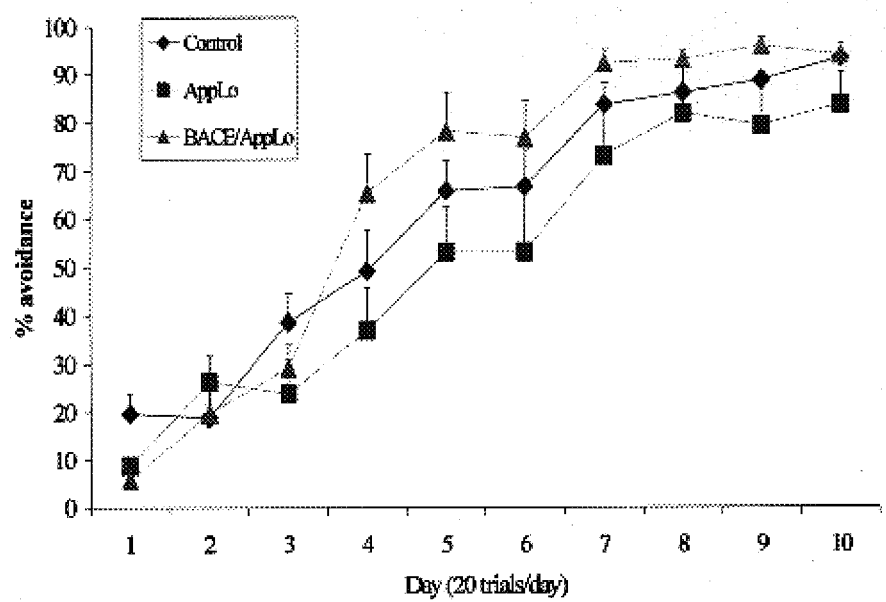

Over the whole test period both male and female mice expressing hAPPLo showed slower learning to avoid the foot shock compared with wild type controls (p=0.003 and p=0.04 respectively) whilst male, but not female mice, expressing hBACE/hAPPLo learnt more quickly (p=0.02 for males, Newman Keuls post hoc following two factor ANOVA with repeated measures)(FIG. 18).

There was no difference in the shock required to elicit any of the behaviours in male mice showing that shock perception did not differ between genotypes. Notably, nor was there a difference in locomotor activity between male wild type and male mice expressing hAPPLo (FIG. 14). Thus, the results in the active avoidance experiment represent a true learning deficit in male mice expressing hAPPLo. However, whilst shock perception did not differ between male wild type and male mice expressing hBACE/hAPPLo, locomotor activity was elevated in the transgenic mice (FIG. 14). Hence, the apparent improvement in active avoidance learning (FIG. 18) could partly be attributed to the hyperactivity of these animals. Similarly, female hAPPLo mice did not differ in their shock threshold nor did they display elevated locomotor activity (FIG. 14) when compared with wild type controls, thus, the active avoidance deficit represents a true learning deficit. However, female mice expressing hBACE/hAPPLo demonstrated an enhanced jump response when compared with wild type controls which could suggest an elevated shock perception and additionally these mice were also hyperactive when compared to wild type controls. Both of these factors could account for the marginal (but non-significant) increase in active avoidance learning seen. Thus, both male and female mice expressing hAPPLo, but not hBACE/hAPPLo, were impaired in active avoidance learning.

C. Summary of the [BACE×APP London] Double Transgenic Mice

It has been shown that the overexpression of human BACE in mice transgenic for human APP London induces An alteration in the APP metabolism toward an increase of sAPP beta fragment associated with a decrease of sAPP alpha fragment. These results have been demonstrated first in organotypic slice cultures of cerebellum coming from 8–10 days old mice; second in brain extracts from adult mice. The methods used were ELISA and western blots.

An increase of amyloid peptides. This effect was demonstrated in organotypic slice cultures, and in brain extracts of adult mice using ELISA, Western Blots and Immunocytochemistry.

An increased pathology as demonstrated in the brain of aging double transgenics by the increase deposition of amyloid peptides (insoluble A-beta peptides) as demonstrated by ELISA and WB, the presence of amyloid plaques and the detection of inflammatory markers as shown by histochemistry and immunohistochemistry.

The results described can be attributed to the expression of hu BACE since similar results have been obtained using 2 parental BACE lines, namely line 13 and line 24. This rules out a possible implication of the transgene integration site.

TABLE 1

Neurological assessment of wild type and mice expressing hAPPLo and hBACE/hAPPLo.

| | | Neurological assessment | Body weight | Body temperature | Grip strength | Horizontal wire | Rotarod −16 rpm | Rotarod −32 rpm |
|---|---|---|---|---|---|---|---|---|
| Male | Wild type | | $44.8 \pm 5.4$ | $38.1 \pm 0.7$ | $157.7 \pm 31$ | 17 (10–31) | 120 (37–120) | 27 (19–45) |
| | hAPPLo | | $41.9 \pm 6.6$ | $37.8 \pm 0.8$ | $145.9 \pm 40.3$ | 16 (6–20) | 33 (8–84) | 10 (5–17)** |
| | hBACE/hAPPLo | | $40.1 \pm 6.8$ | $38.3 \pm 0.8$ | $125.1 \pm 20.3$* | 9 (4–13)* | 26 (4–120) | 11 (1–38) |
| Female | Wild type | | $33.4 \pm 2.7$ | $38.5 \pm 0.7$ | $139.2 \pm 10.7$ | 25 (18–32) | 120 (110–120) | 54 (33–63) |
| | hAPPLo | | $36.2 \pm 8.3$ | $38.1 \pm 0.7$ | $116.4 \pm 18.7$** | 18 (11–31)** | 53 (4–103) | 15 (2–54) |
| | hBACE/hAPPLo | | $31.6 \pm 9.7$ | $38.0 \pm 0.7$ | $141.8 \pm 37.7$ | 3 (1–15)** | 120 (61–120) | 30 (12–88) |

Data are presented as mean ± s.e.m. (unpaired t test), median with interquartile range in parentheses (Mann Whitney U test): *p < 0.05, **p < 0.01.

TABLE 2

Shock threshold study in mice expressing hAPPLo and hBACE/hAPPLo and wild type controls.

| | Shock Threshold (mA) | Minimum shock (mA) required to elicit a flinch response | Minimum shock (mA) required to elicit a jump response | Minimum shock (mA) required to elicit vocalisations |
|---|---|---|---|---|
| Male | Wild type | 0.3 (0.3–0.4) | 0.5 (0.4–0.5) | 0.6 (0.5–0.8) |
| | hAPPLo | 0.3 (0.3–0.4) | 0.5 (0.4–0.7) | 0.6 (0.5–0.6) |
| | hBACE/hAPPLo | 0.2 (0.2–0.3) | 0.4 (0.3–0.5) | 0.5 (0.3–0.5) |
| Female | Wild type | 0.3 (0.2–0.4) | 0.6 (0.5–0.8) | 0.5 (0.3–0.6) |
| | hAPPLo | 0.2 (0.2–0.3) | 0.4 (0.2–0.5) | 0.3 (0.2–0.5) |
| | hBACE/hAPPLo | 0.2 (0.2–0.3) | 0.3 (0.3–0.4)** | 0.4 (0.3–0.6) |

Data are presented as median with interquartile range in parentheses (Kruskal Wallis, followed where appropriate with a Mann Whitney U test with wild type mice as the control group): **$p < 0.01$.

What is claimed is:

1. A method of producing a double transgenic mouse whose genome incorporates DNA comprising a coding sequence encoding SEQ ID NO. 9 operably linked to a prion regulatory promoter sequence and a coding sequence which encodes SEQ ID NO. 1 operably linked to a Thy-1 regulatory promoter sequence, which method comprises:

(a) introducing a DNA construct comprising a coding sequence which encodes SEQ ID NO. 9 and a prion regulatory sequence operably linked to the coding sequence into a mouse cell or embryo and generating a transgenic mouse from said cell or embryo;

(b) introducing a DNA construct comprising a coding sequence which encodes SEQ ID NO. 1 and a Thy-1 regulatory sequence operably linked to the coding sequence into a mouse cell or embryo and generating a transgenic mouse from said cell or embryo; and (c) crossbreeding the transgenic mice generated in steps (a) and (b);

wherein the double transgenic mouse exhibits increased pathology as demonstrated by increased deposition of A-beta peptide relative to an APP London single transgenic mouse.

2. A method of producing a double transgenic mouse whose genome incorporates DNA comprising a coding sequence encoding SEQ ID NO. 9 operably linked to a prion regulatory promoter sequence and a coding sequence which encodes SEQ ID NO. 1 operably linked to a Thy-1 regulatory promoter sequence, which method comprises:

(a) co-injecting into a mouse cell or embryo: (1) a DNA construct comprising a coding sequence encoding SEQ ID NO. 9 operably linked to a prion regulatory promoter sequence; and (2) a DNA construct comprising a coding sequence which encodes SEQ ID NO. 1 operably linked to a Thy-1 regulatory promoter sequence; and (b) generating a double transgenic mouse from said cell or embryo;

wherein the double transgenic mouse exhibits increased pathology as demonstrated by increased deposition of A-beta peptide relative to an APP London single transgenic mouse.

3. The method according to claim 2, wherein the two DNA constructs in step (a) are linked in a single vector prior to co-injecting into said mouse cell or embryo.

4. The method according to claim 2, wherein the two DNA constructs in step (a) are separated in two different vectors prior to co-injecting into said mouse cell or embryo.

5. A double transgenic mouse whose genome incorporates DNA comprising: (1) a coding sequence which encodes SEQ ID NO. 1 operably linked to a Thy-1 regulatory sequence and (2) a coding sequence encoding SEQ ID NO.

9 operably linked to a prion regulatory sequence; wherein the double transgenic mouse exhibits increased pathology as demonstrated by increased deposition of A-beta peptide relative to an APP London single transgenic mouse.

6. The double transgenic mouse according to claim 5, exhibiting one or more histopathologies similar to those of Alzheimer's disease.

7. A descendant of the double transgenic mouse according to claim 5, wherein said descendant is obtained by breeding said double transgenic mouse with a mouse that exhibits a phenotype that is the same as the double transgenic mouse or that exhibits a phenotype that is different from the phenotype of the double transgenic mouse, wherein the descendant of the double transgenic mouse exhibits increased pathology as demonstrated by increased deposition of A-beta peptide relative to an APP London single transgenic mouse.

8. A cell line or primary cell culture derived from a double transgenic mouse according to claim 5, or its descendants according to claim 7.

9. An organotypic brain slice culture derived from a double transgenic mouse according to claim 5, or its descendants according to claim 7.

* * * * *

UNITED STATES PATENT AND TRADEMARK OFFICE
CERTIFICATE OF CORRECTION

| | |
|---|---|
| PATENT NO. | : 7,247,766 B2 |
| APPLICATION NO. | : 10/372730 |
| DATED | : July 24, 2007 |
| INVENTOR(S) | : Jacobsen et al. |

It is certified that error appears in the above-identified patent and that said Letters Patent is hereby corrected as shown below:

TITLE PAGE (54) and column 1 lines 1-3:

The title reads "DOUBLE TRANSGENIC MICE OVEREXRESSING HUMAN BETA SECRETASE AND HUMAN APP-LONDON". The title should read -- DOUBLE TRANSGENIC MICE OVEREXPRESSING HUMAN BETA SECRETASE AND HUMAN APP-LONDON --.

Signed and Sealed this

Ninth Day of October, 2007

JON W. DUDAS
*Director of the United States Patent and Trademark Office*

SEQUENCE LISTING

<160> NUMBER OF SEQ ID NOS: 19

<210> SEQ ID NO 1
<211> LENGTH: 4742
<212> TYPE: DNA
<213> ORGANISM: Homo sapiens

<400> SEQUENCE: 1

```
gtcgacggat agctttgctc tagactggaa ttcgggcgcg atgctgcccg gtttggcact      60
gctcctgctg gccgcctgga cggctcgggc gctggaggta cccactgatg gtaatgctgg     120
cctgctggct gaaccccaga ttgccatgtt ctgtggcaga ctgaacatgc acatgaatgt     180
ccagaatggg aagtgggatt cagatccatc agggaccaaa acctgcattg ataccaagga     240
aggcatcctg cagtattgcc aagaagtcta ccctgaactg cagatcacca atgtggtaga     300
agccaaccaa ccagtgacca tccagaactg gtgcaagcgg ggccgcaagc agtgcaagac     360
ccatccccac tttgtgattc cctaccgctg cttagttggt gagtttgtaa gtgatgccct     420
tctcgttcct gacaagtgca aattcttaca ccaggagagg atggatgttt gcgaaactca     480
tcttcactgg cacaccgtcg ccaaagagac atgcagtgag aagagtacca acttgcatga     540
ctacggcatg ttgctgccct gcggaattga caagttccga ggggtagagt tgtgtgttg     600 cccactggct gaagaaagtg acaatgtgga ttctgctgat gcggaggagg atgactcgga     660
tgtctggtgg ggcggagcag acacagacta tgcagatgga tccgaagaca aagtagtaga     720
agtagcagag gaggaagaag tggctgaggt ggaagaagaa gaagccgatg atgacgagga     780
cgatgaggat ggtgatgagg tagaggaaga ggctgaggaa ccctacgaag aagccacaga     840
gagaaccacc agcattgcca ccaccaccac caccaccaca gagtctgtgg aagaggtggt     900
tcgaggtaat ccaccatttg cttggattcc ccccaccccc aaggaaaaga agcgtaata      960 ccagagttgg aaatatccac cctagcacca ctgccttccc caatcaaaaa catgttttt     1020 tttccaaaag gcttcttatg cttgtgaaat ttttttggtt taacaagcaa acaatttcaa    1080
ataatgtgaa atctttatta tacagtttgt tttgtacctt gtatatgctg cttggcaaat    1140
cccaagttaa ttctacaaga ctccgcccaa ccaggtagtc atctaatttg acaaacactg    1200
agttaggtga ctccttggta ttcctttggc agtgagtgtt tgttatataa tattgtctgt    1260
taccacctag acgatgctct gagaggtgta aatctctagt cctggtggcc agttaaattc    1320
```

```
ctcagtaaat gtttggtaga tgctgcctaa taaaccagtc caggttgcca ctgggaggat    1380
taaaagaagt aaacgtgtat acatgaacag agagacagtg cctttcatg  ctaaatgtgg    1440 ttccccacat ctcctctgat tagaggtgtg ctctgaacaa gccgagacgg ggccgtgccg    1500
agcaatgatc tcccgctggt actttgatgt gactgaaggg aagtgtgccc cattctttta    1560
cggcggatgt ggcggcaacc ggaacaactt tgacacagaa gagtactgca tggccgtgtg    1620
tggcagcgcc agtaagtgga cccttcttcg agcctggcca cctttcgtct ctctcgccac    1680
tgactctgct ttttgtaaca gattgatttc ctggttcttg ggaatgggcc tgttgctacc    1740
actaaccaca tttctgtcca cttctctaat tgctcagagt ctccgcagta tgttcaatca    1800
tgagcacacc tctccgtctt tccctgataa agcatggcca tggatgtgtt ctcttcctag    1860
ctgtagcaca tatgtcttgc aatccagagg acttttgag  tgcttctctt ttaaacaaag    1920
ctggagtggc tgttttgtct tctgcaggtc aacttcttac gaaaatagat cttatgttta    1980
tatgttcatt ttggttttgt tggagggacc aaacctaagt gagtgatttt gtttgttagg    2040 ttgtttttt  gtcagtggac tcgtgcattt cagccatcat tcccatgttt ctctttttgt    2100
ttttagttat gttctcttat tttttccata gtgtcccaaa gtttactcaa gactacccag    2160
gaacctcttg cccgagatcc tgttaaacgt acgttgtcat tcacctgagg aagggaaga    2220 ggggaggagg atgctgcttg gttcacataa ctccagcatc atcaccttct ttgcatggtt    2280
ttgtgtttct tgaacacctg tcttagtaaa atgtttcttc ccattacctt gcttgtaatt    2340
acatctgatt ttgccagaca gcttgagatg ttgggctaag aacatcattg actaagtttc    2400
ttctatttct gaccaatttc ctttttattt agtctggttt tattgaatat tatgtggaca    2460
acatcattgt attgtatttg ccattactat tttatttcct aaaagctctc agtgtaactg    2520
agagcaggct tagcctctca ctgcttttgc agaactgaag aacaagggct aggtgcagtg    2580
gaaggaaagt gactttactt agcaaagcta gcaatgggga aatggtccag gctcctgcct    2640
taaagcaacc atctcaaatt ttggattaaa aaacaaaggc ttaaaagggg gagcttggaa    2700
tgcagggcat gaaggagggg tgaggaggtg ctgctataca ggacttgttc caaagacttg    2760
agttattatc cagttcggta agtgggctgg cgcatcccgc acaatcgggt tgtaaattaa    2820
ctgcagcctt gaggtgatct cctgatgagg gagaattcat tgactattgt caaatttatg    2880
aagacagaaa agtcctttg  tgattcaaaa atgtgtttat tgatgtttat atatcttttg    2940
tagtgtttcc catactgtct catgaaggtt gtcttcgtaa ttcagttatc taaaatacat    3000
cctacaattt accttttccc tgggggttgc cgtttattcc tacaacaggc taattacaga    3060
atatctggtg gtttctgcag gagtcttagt gttatgatat tgatgatatc atccatttac    3120
tttcaaaatt ggcaaaataa ataattttag gaaagccatg gggatttgga aaaacatgtc    3180
ttcagcacca actgtttttg ctctttgcat gcttgtttcg taaagaactc taatgctata    3240
attgcaaaat ggaccatttt aaagatttt  ccttcattct gtacttggga gtggtgaaag    3300
acatccttac tgtgctgcac agtgtctcat ggtgttctct taaacagcat taacgtcttg    3360
tatgcgctgc tttactaaat tctctgttct gagaaataac tgaaaatacg ctttctatt    3420 aaacgagtgg attattctgt tgttgttggc ttttttttct caaacctcct tctcttctac    3480
tttatagttc ctacaacagc agccagtacc cctgatgccg ttgacaagta tctcgagaca    3540
cctggggatg agaatgaaca tgcccatttc cagaaagcca agagaggct  tgaggccaag    3600 caccgagaga gaatgtccca ggtcatgaga gaatgggaag aggcagaacg tcaagcaaag    3660
aacttgccta agctgataaa gaaggcagtt atccagcatt tccaggagaa agtggaatct    3720
```

-continued

```
ttggaacagg aagcagccaa cgagagacag cagctggtgg agacacacat ggccagagtg    3780
gaagccatgc tcaatgaccg ccgccgcctg gccctggaga actacatcac cgctctgcag    3840
gctgttcctc ctcggcctcg tcacgtgttc aatatgctaa agaagtatgt ccgcgcagaa    3900
cagaaggaca gacagcacac cctaaagcat ttcgagcatg tgcgcatggt ggatcccaag    3960
aaagccgctc agatccggtc ccaggttatg acacacctcc gtgtgattta tgagcgcatg    4020
aatcagtctc tctccctgct ctacaacgtg cctgcagtgg ccgaggagat tcaggatgaa    4080
gttgatgagc tgcttcagaa agagcaaaac tattcagatg acgtcttggc caacatgatt    4140
agtgaaccaa ggatcagtta cggaaacgat gctctcatgc catctttgac cgaaacgaaa    4200
accaccgtgg agctccttcc cgtgaatgga gagttcagcc tggacgatct ccagccgtgg    4260
cattcttttg gggctgactc tgtgccagcc aacacagaaa cgaagttga gcctgttgat     4320 gcccgccctg ctgccgaccg aggactgacc actcgaccag ttctgggtt gacaaatatc     4380 aagacggagg agatctctga agtgaagatg gatgcagaat ccgacatga ctcaggatat     4440 gaagttcatc atcaaaaatt ggtgttcttt gcagaagatg tgggttcaaa caaaggtgca    4500
atcattggac tcatggtggg cggtgttgtc atagcgacag tgatcttcat caccttggtg    4560
atgctgaaga gaaacagta cacatccatt catcatggtg tggtggaggt tgacgccgct     4620 gtcacccag aggagcgcca cctgtccaag atgcagcaga acggctacga aaatccaacc     4680
tacaagttct tgagcagat gcagaactag acccccgcca cagaagctgg gaattcatcg     4740
at                                                                  4742
```

<210> SEQ ID NO 2
<211> LENGTH: 25
<212> TYPE: DNA
<213> ORGANISM: Mus musculus

<400> SEQUENCE: 2
acgtaatgaa gtcacccagc aggag                                          25

<210> SEQ ID NO 3
<211> LENGTH: 25
<212> TYPE: DNA
<213> ORGANISM: Homo sapiens

<400> SEQUENCE: 3
ggttctctct gtggcttctt cgtag                                          25

<210> SEQ ID NO 4
<211> LENGTH: 25
<212> TYPE: DNA
<213> ORGANISM: Homo sapiens

<400> SEQUENCE: 4
aagtatgtcc gcgcagaaca gaagg                                          25

<210> SEQ ID NO 5
<211> LENGTH: 25
<212> TYPE: DNA
<213> ORGANISM: Mus musculus

<400> SEQUENCE: 5
ggttctctct gtggcttctt cgtag                                          25

<210> SEQ ID NO 6

```
<211> LENGTH: 60
<212> TYPE: DNA
<213> ORGANISM: Homo sapiens

<400> SEQUENCE: 6
gtttaacagg atctcgggca agaggttcct gggtagtctt gagtaaactt tgggacatgg      60

<210> SEQ ID NO 7
<211> LENGTH: 60
<212> TYPE: DNA
<213> ORGANISM: Homo sapiens

<400> SEQUENCE: 7
cgctgccaca cacggccatg cagtactctt ctgtgtcaaa gttgttccgg ttgccgccac      60

<210> SEQ ID NO 8
<211> LENGTH: 1506
<212> TYPE: DNA
<213> ORGANISM: Homo sapiens

<400> SEQUENCE: 8
atggcccaag ccctgccctg gctcctgctg tggatgggcg cgggagtgct gcctgcccac      60
ggcacccagc acggcatccg actgccactg cgcagcggac tgggaggtgc acctctggga     120
ctgcggctgc cccgggagac cgacgaagag cccgaggagc ccggccggag gggcagcttt     180
gtggagatgg tggacaacct gaggggcaag tcggggcagg gctactacgt ggagatgacc     240
gtgggcagcc ccccgcagac gctcaacatc tggtggata caggcagcag taactttgca     300
gtgggtgctg ccccccaccc cttcctgcat cgctactacc agaggcagct gtccagcaca     360
taccgggacc tccggaaggg tgtgtatgag ccctacaccc agggcaagtg ggaaggggag     420
ctgggcaccg acctggtaag catcccccat ggccccaacg tcactgtgcg tgccaacatt     480
gctgccatca ctgaatcaga caagttcttc atcaacggct ccaactggga aggcatcctg     540
gggctggcct atgctgagat tgccaggcct gacgactccc tggagccttt ctttgactct     600
ctggtaaagc agaccacgt tcccaacctc ttctccctgc agctttgtgg tgctggcttc     660
cccctcaacc agtctgaagt gctggcctct gtcggaggga gcatgatcat tggaggtatc     720
gaccactcgc tgtacacagg cagtctctgg tatacaccca tccggcggga gtggtattat     780
gaggtgatca ttgtgcgggt ggagatcaat ggacaggatc tgaaaatgga ctgcaaggag     840
tacaactatg acaagagcat tgtggacagt ggcaccacca accttcgttt gcccaagaaa     900
gtgtttgaag ctgcagtcaa atccatcaag gcagcctcct ccacggagaa gttccctgat     960
ggtttctggc taggagagca gctggtgtgc tggcaagcag gcaccacccc ttggaacatt    1020
ttcccagtca tctcactcta cctaatgggt gaggttacca ccagtccttt ccgcatcacc    1080
atccttccgc agcaatacct gcggccagtg aagatgtgg ccacgtccca agacgactgt    1140
tacaagtttg ccatctcaca gtcatccacg ggcactgtta tgggagctgt tatcatggag    1200
ggcttctacg ttgtctttga tcgggcccga aaacgaattg ctttgctgt cagcgcttgc    1260 catgtgcacg atgagttcag gacggcagcg gtggaaggcc ttttgtcac cttgacatg     1320 gaagactgtg gctacaacat tccacagaca gatgagtcaa ccctcatgac catagcctat    1380
gtcatggctg ccatctgcgc cctcttcatg ctgccactct gcctcatggt gtgtcagtgg    1440
cgctgcctcc gctgcctgcg ccagcagcat gatgactttg ctgatgacat ctccctgctg    1500
aagtga                                                                1506
```

```
<210> SEQ ID NO 9
<211> LENGTH: 501
<212> TYPE: PRT
<213> ORGANISM: Homo sapiens

<400> SEQUENCE: 9
```

| | | | | | | | | | | | | | | |
|---|---|---|---|---|---|---|---|---|---|---|---|---|---|---|
| Met | Ala | Gln | Ala | Leu | Pro | Trp | Leu | Leu | Leu | Trp | Met | Gly | Ala | Gly | Val |
| 1 | | | | 5 | | | | | 10 | | | | | 15 |

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Glu Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro
        195                 200                 205

Asn Leu Phe Ser Leu Gln Leu Cys Gly Ala Gly Phe Pro Leu Asn Gln
    210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
    290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
        355                 360                 365

Pro Val Glu Asp Val Ala Thr Ser Gln Asp Asp Cys Tyr Lys Phe Ala
    370                 375                 380

```
Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
            405                 410                 415

Val Ser Ala Cys His Val His Asp Glu Phe Arg Thr Ala Ala Val Glu
        420                 425                 430

Gly Pro Phe Val Thr Leu Asp Met Glu Asp Cys Gly Tyr Asn Ile Pro
        435                 440                 445

Gln Thr Asp Glu Ser Thr Leu Met Thr Ile Ala Tyr Val Met Ala Ala
    450                 455                 460

Ile Cys Ala Leu Phe Met Leu Pro Leu Cys Leu Met Val Cys Gln Trp
465                 470                 475                 480

Arg Cys Leu Arg Cys Leu Arg Gln Gln His Asp Asp Phe Ala Asp Asp
                485                 490                 495

Ile Ser Leu Leu Lys
            500

<210> SEQ ID NO 10
<211> LENGTH: 24
<212> TYPE: DNA
<213> ORGANISM: Mus musculus

<400> SEQUENCE: 10
ttcaaccgag ctgaagcatt ctcc                                        24

<210> SEQ ID NO 11
<211> LENGTH: 23
<212> TYPE: DNA
<213> ORGANISM: Homo sapiens

<400> SEQUENCE: 11
agggagtcgt caggcctggc aat                                         23

<210> SEQ ID NO 12
<211> LENGTH: 21
<212> TYPE: DNA
<213> ORGANISM: Homo sapiens

<400> SEQUENCE: 12
gtgggcagcc ccccgccaga c                                           21

<210> SEQ ID NO 13
<211> LENGTH: 23
<212> TYPE: DNA
<213> ORGANISM: Homo sapiens

<400> SEQUENCE: 13
ccgacagagg ccagcacttc aga                                         23

<210> SEQ ID NO 14
<211> LENGTH: 21
<212> TYPE: DNA
<213> ORGANISM: Mus musculus

<400> SEQUENCE: 14
tgtagtggca aagtggagat t                                           21

<210> SEQ ID NO 15
<211> LENGTH: 20
<212> TYPE: DNA
<213> ORGANISM: Mus musculus
```

```
<400> SEQUENCE: 15
gtggtgcagg atgcattgct                                                 20

<210> SEQ ID NO 16
<211> LENGTH: 60
<212> TYPE: DNA
<213> ORGANISM: Homo sapiens

<400> SEQUENCE: 16
aggggcagcc ggatgccgtg ctgggtgccg tgggcaggca gcactcccgc gcccatccac     60

<210> SEQ ID NO 17
<211> LENGTH: 60
<212> TYPE: DNA
<213> ORGANISM: Homo sapiens

<400> SEQUENCE: 17
aggttgggaa cgtgggtctg ctttaccaga gagtcaaaga aaggctccag ggagtcgtca     60

<210> SEQ ID NO 18
<211> LENGTH: 60
<212> TYPE: DNA
<213> ORGANISM: Homo sapiens

<400> SEQUENCE: 18
aaagccaatt cgttttcggg cccgatcaaa gacaacgtag aagccctcca tgataacagc    60

<210> SEQ ID NO 19
<211> LENGTH: 60
<212> TYPE: DNA
<213> ORGANISM: Mus musculus

<400> SEQUENCE: 19
ccagggagga agaggatgcg gcagtggcca tctcctgctc gaagtctaga gcaacatagc    60
```